(12) United States Patent
Labarriere et al.

(10) Patent No.: US 8,604,166 B2
(45) Date of Patent: Dec. 10, 2013

(54) MELANOMA ANTIGEN PEPTIDE AND USES THEREOF

(75) Inventors: Nathalie Labarriere, Nantes Cedex 1 (FR); Agnes Moreau-Aubry, Nantes Cedex 1 (FR); Yann Godet, Nantes Cedex 1 (FR)

(73) Assignees: Inserm (Institut National de la Sante et de la Recherche Medicale), Paris (FR); Universite de Nantest, Nantes (FR); Chu Nantes, Nantes (FR)

( * ) Notice: Subject to any disclaimer, the term of this patent is extended or adjusted under 35 U.S.C. 154(b) by 180 days.

(21) Appl. No.: 13/060,484

(22) PCT Filed: Sep. 2, 2009

(86) PCT No.: PCT/EP2009/061354
§ 371 (c)(1),
(2), (4) Date: May 9, 2011

(87) PCT Pub. No.: WO2010/026165
PCT Pub. Date: Mar. 11, 2010

(65) Prior Publication Data
US 2011/0212098 A1 Sep. 1, 2011

(30) Foreign Application Priority Data
Sep. 2, 2008 (EP) .................................. 08305517

(51) Int. Cl.
*C07K 7/00* (2006.01)

(52) U.S. Cl.
USPC .......... 530/328; 530/324; 530/325; 530/326; 530/327

(58) Field of Classification Search
None
See application file for complete search history.

(56) References Cited

FOREIGN PATENT DOCUMENTS

WO   96/21734   7/1996

OTHER PUBLICATIONS

Godet et al, J. Exp. Med. vol. 205 p. 2673 (2008).*
Engelhard, Current Opinion in Immunology vol. 6 p. 13 (1994).*
Guo, et al Nature vol. 360 p. 384 (1992).*
Rammensee et al, Immunogenetics vol. 41 p. 178 (1995).*
Shastri et al J. Immunol. vol. 1995 vol. 155 p. 4339.*
Godet et al., J. Exp. Med., 205:2673-2682 (2008).
International Search Report in PCT/EP09/61354, dated Dec. 17, 2009.
Taus et al., J. Gen. Virol., 88:40-45 (2007).
Written Opinion in PCT/EP09/61354, dated Dec. 17, 2009.

* cited by examiner

*Primary Examiner* — Sheela J Huff
(74) *Attorney, Agent, or Firm* — McAndrews, Held & Malloy, Ltd.

(57) ABSTRACT

The present invention relates to novel melanoma antigen peptides and specific T lymphocytes directed to said peptides and the use thereof for treating melanoma.

5 Claims, 11 Drawing Sheets

SEQUENCE LISTING

<160> NUMBER OF SEQ ID NOS: 42

<210> SEQ ID NO 1
<211> LENGTH: 2154
<212> TYPE: DNA

<213> ORGANISM: homo sapiens

<400> SEQUENCE: 1

```
atccccaccc acccggctcc caggatcctc attaggaagc cctcaggagc cctggggtgg      60
gtctccttgc cctgtgaacg ctccatttgt gttattgaat ccaacataaa tgcagcattg     120
tcttcagagg tgagcaatgg ccgtggccgg aggtgcgcat gggatgcagg cggcgtgtgc     180
tgctgttgat tttctctgct ctgctcttag cttactttag cagatagtgg agtttcacgt     240
ggcagtccgg taaaccaagg cagtgtgaac atcccttccc cacaatgagt gaaaatgcag     300
gaggtgccgt agcgagaaca cgacagcat tctgcgcatt ggtgagcccg actccccagc     360
ctcggtgccc accgaagccc cctctggctg cactgtgcca gtgagtccag gctccttctc     420
agcagaaggt ggctgctctg cagggcccct cgcctccctg ctcctcaggg acccgcact     480
cttccatgtc cgtagggaga cgcgcaccga gctggagaca cagatctgcg aggagtaact     540
tgcctctctc accagcactg ccaggggcgg atcagcgcca gcaccttcca gcatgcgcta     600
aactgctgga gaagctggag tggctggaag gagccctgcc tgcctgccct cctcctcctc     660
agttgctggc cttggcagct ctagggtgac ccagcagggg cctggaggag taggaagcag     720
cttcccagct gcagtctgca tcatcctctc tgtgctgtca cagaatggaa ggttttagca     780
gaaaaaggag tttgtaagcg acattcagaa gatttgggca gcagtttctt ccccccatagg    840
gtcctgtctt ttgggagtgg ggagtgctgg gccaggctgc tcgctggctg tttcacaggt     900
ggtggaattt aagagcagac ttgggtcgag ctgtgaccgt tcaggtgatg cacgcacagg     960
aggttcagct gtgtgcctgt gaggcaggca ggagcgtcac ccaagcttca aagagaatt    1020
ccccggcagc agcgtggcgc tcagcatgtt ccgtgtctga ctgttttgat tgtctctcag    1080
tccagttgac aaattccttt taagatgaaa tttgaattaa tttgcagaac ttgtacaaat    1140
ctccaagaaa acagcttaag gaacagatta aagaatgaat gccttaggaa ttaaagcatt    1200
aatagctctt gagtagactg gatggaaaga tgagttgtgt aggttatcca gatgaggcta    1260
catccaggga gcaattctta ccttcagagg gcgctgcctg tcctccttgg catccaagtg    1320
agcgcatctc ctccacgctc aatgatgaat gctggccggc atccctgtga ggaaccttgt    1380
gatcattttc catttctgaa aactcccagg tggtgggggc ccttggccca catcagcatt    1440
gaccaccccg ggctcagatc tggccaggtg cctgcgttgt gatgggaatt tcagtacact    1500
gaattttgcc tctgaccctg atgaaatagc ttcggtggca tttgcatcaa gatcatgtta    1560
gtgtcatctc tattagatgc tttggagcaa acatgaactt gggtttcctt ttaagatgtc    1620
ctgtgattcc agattcaggg gaatctgaga aaagtttgaa gaaagaaaat tccactcggc    1680
cagccaacct tgggtgtgca gagcctgccc cgccttcccc actttgtcct gagaagctgg    1740
gtcctcccca gcaccagagt tgctgctgct tcccctcgcg ctcttggctg ctctcccggc    1800
cccaagcctg agtgacactc taggattgca gatggcaggc tggtctctgg ctccccgt     1860
ccccatgacc ctccacctgc acccagacct ctgggtcctt gctcaggcag cccctgccct    1920
cggtgagacg cagcccactg tgggcccttc cctgggcct gccatcagct cctgtgctcc    1980
tcggcgcccc agcggctgcc ctgggcccgt tcccacagca cctggcacac agcaggagcc    2040
atgaatgttc tttgggaact gaatgaggag tggaaatgcg gcatgtcat gttttttgaag   2100
ttaataaaaa aaatccctta aaagttgaaa aaaaaaaaaa aaaaaaaaaa aaaa          2154
```

<210> SEQ ID NO 2
<211> LENGTH: 9
<212> TYPE: PRT

-continued

```
<213> ORGANISM: artificial
<220> FEATURE:
<223> OTHER INFORMATION: melanoma antigen peptide 1
<220> FEATURE:
<221> NAME/KEY: MISC_FEATURE
<222> LOCATION: (2)..(2)
<223> OTHER INFORMATION: X is L, M, V, I or Q
<220> FEATURE:
<221> NAME/KEY: MISC_FEATURE
<222> LOCATION: (9)..(9)
<223> OTHER INFORMATION: X is A, V or L

<400> SEQUENCE: 2

Thr Xaa Asn Asp Glu Cys Trp Pro Xaa
1               5

<210> SEQ ID NO 3
<211> LENGTH: 9
<212> TYPE: PRT
<213> ORGANISM: artificial
<220> FEATURE:
<223> OTHER INFORMATION: melanoma antigen peptide 2
<220> FEATURE:
<221> NAME/KEY: MISC_FEATURE
<222> LOCATION: (2)..(2)
<223> OTHER INFORMATION: X is C, L, M, V, I or Q
<220> FEATURE:
<221> NAME/KEY: MISC_FEATURE
<222> LOCATION: (9)..(9)
<223> OTHER INFORMATION: X is A, V or L

<400> SEQUENCE: 3

Arg Xaa Pro Pro Lys Pro Pro Leu Xaa
1               5

<210> SEQ ID NO 4
<211> LENGTH: 46
<212> TYPE: PRT
<213> ORGANISM: artificial
<220> FEATURE:
<223> OTHER INFORMATION: MELOE-1

<400> SEQUENCE: 4

Met Ser Cys Val Gly Tyr Pro Asp Glu Ala Thr Ser Arg Glu Gln Phe
1               5                   10                  15

Leu Pro Ser Glu Gly Ala Ala Cys Pro Pro Trp His Pro Ser Glu Arg
            20                  25                  30

Ile Ser Ser Thr Leu Asn Asp Glu Cys Trp Pro Ala Ser Leu
        35                  40                  45

<210> SEQ ID NO 5
<211> LENGTH: 39
<212> TYPE: PRT
<213> ORGANISM: artificial
<220> FEATURE:
<223> OTHER INFORMATION: MELOE-2

<400> SEQUENCE: 5

Met Ser Glu Asn Ala Gly Gly Ala Val Ala Arg Thr Ala Thr Ala Phe
1               5                   10                  15

Cys Ala Leu Val Ser Pro Thr Pro Gln Pro Arg Cys Pro Lys Pro
            20                  25                  30

Pro Leu Ala Ala Leu Cys Gln
        35

<210> SEQ ID NO 6
<211> LENGTH: 9
<212> TYPE: PRT
```

-continued

```
<213> ORGANISM: artificial
<220> FEATURE:
<223> OTHER INFORMATION: melanoma antigen peptide 1

<400> SEQUENCE: 6

Thr Leu Asn Asp Glu Cys Trp Pro Ala
1               5

<210> SEQ ID NO 7
<211> LENGTH: 9
<212> TYPE: PRT
<213> ORGANISM: artificial
<220> FEATURE:
<223> OTHER INFORMATION: melanoma antigen peptide 1

<400> SEQUENCE: 7

Thr Met Asn Asp Glu Cys Trp Pro Ala
1               5

<210> SEQ ID NO 8
<211> LENGTH: 9
<212> TYPE: PRT
<213> ORGANISM: artificial
<220> FEATURE:
<223> OTHER INFORMATION: melanoma antigen peptide 1

<400> SEQUENCE: 8

Thr Val Asn Asp Glu Cys Trp Pro Ala
1               5

<210> SEQ ID NO 9
<211> LENGTH: 9
<212> TYPE: PRT
<213> ORGANISM: artificial
<220> FEATURE:
<223> OTHER INFORMATION: melanoma antigen peptide 1

<400> SEQUENCE: 9

Thr Ile Asn Asp Glu Cys Trp Pro Ala
1               5

<210> SEQ ID NO 10
<211> LENGTH: 9
<212> TYPE: PRT
<213> ORGANISM: artificial
<220> FEATURE:
<223> OTHER INFORMATION: melanoma antigen peptide 1

<400> SEQUENCE: 10

Thr Gln Asn Asp Glu Cys Trp Pro Ala
1               5

<210> SEQ ID NO 11
<211> LENGTH: 9
<212> TYPE: PRT
<213> ORGANISM: artificial
<220> FEATURE:
<223> OTHER INFORMATION: melanoma antigen peptide 1

<400> SEQUENCE: 11

Thr Leu Asn Asp Glu Cys Trp Pro Val
1               5

<210> SEQ ID NO 12
<211> LENGTH: 9
<212> TYPE: PRT
<213> ORGANISM: artificial
<220> FEATURE:
```

-continued

<223> OTHER INFORMATION: melanoma antigen peptide 1

<400> SEQUENCE: 12

Thr Met Asn Asp Glu Cys Trp Pro Val
1               5

<210> SEQ ID NO 13
<211> LENGTH: 9
<212> TYPE: PRT
<213> ORGANISM: artificial
<220> FEATURE:
<223> OTHER INFORMATION: melanoma antigen peptide 1

<400> SEQUENCE: 13

Thr Val Asn Asp Glu Cys Trp Pro Val
1               5

<210> SEQ ID NO 14
<211> LENGTH: 9
<212> TYPE: PRT
<213> ORGANISM: artificial
<220> FEATURE:
<223> OTHER INFORMATION: melanoma antigen peptide 1

<400> SEQUENCE: 14

Thr Ile Asn Asp Glu Cys Trp Pro Val
1               5

<210> SEQ ID NO 15
<211> LENGTH: 9
<212> TYPE: PRT
<213> ORGANISM: artificial
<220> FEATURE:
<223> OTHER INFORMATION: melanoma antigen peptide 1

<400> SEQUENCE: 15

Thr Gln Asn Asp Glu Cys Trp Pro Val
1               5

<210> SEQ ID NO 16
<211> LENGTH: 9
<212> TYPE: PRT
<213> ORGANISM: artificial
<220> FEATURE:
<223> OTHER INFORMATION: melanoma antigen peptide 1

<400> SEQUENCE: 16

Thr Leu Asn Asp Glu Cys Trp Pro Leu
1               5

<210> SEQ ID NO 17
<211> LENGTH: 9
<212> TYPE: PRT
<213> ORGANISM: artificial
<220> FEATURE:
<223> OTHER INFORMATION: melanoma antigen peptide 1

<400> SEQUENCE: 17

Thr Met Asn Asp Glu Cys Trp Pro Leu
1               5

<210> SEQ ID NO 18
<211> LENGTH: 9
<212> TYPE: PRT
<213> ORGANISM: artificial
<220> FEATURE:
<223> OTHER INFORMATION: melanoma antigen peptide 1

```
<400> SEQUENCE: 18

Thr Val Asn Asp Glu Cys Trp Pro Leu
1               5

<210> SEQ ID NO 19
<211> LENGTH: 9
<212> TYPE: PRT
<213> ORGANISM: artificial
<220> FEATURE:
<223> OTHER INFORMATION: melanoma antigen peptide 1

<400> SEQUENCE: 19

Thr Ile Asn Asp Glu Cys Trp Pro Leu
1               5

<210> SEQ ID NO 20
<211> LENGTH: 9
<212> TYPE: PRT
<213> ORGANISM: artificial
<220> FEATURE:
<223> OTHER INFORMATION: melanoma antigen peptide 1

<400> SEQUENCE: 20

Thr Gln Asn Asp Glu Cys Trp Pro Leu
1               5

<210> SEQ ID NO 21
<211> LENGTH: 9
<212> TYPE: PRT
<213> ORGANISM: artificial
<220> FEATURE:
<223> OTHER INFORMATION: melanoma antigen peptide 2

<400> SEQUENCE: 21

Arg Cys Pro Pro Lys Pro Pro Leu Ala
1               5

<210> SEQ ID NO 22
<211> LENGTH: 9
<212> TYPE: PRT
<213> ORGANISM: artificial
<220> FEATURE:
<223> OTHER INFORMATION: melanoma antigen peptide 2

<400> SEQUENCE: 22

Arg Leu Pro Pro Lys Pro Pro Leu Ala
1               5

<210> SEQ ID NO 23
<211> LENGTH: 9
<212> TYPE: PRT
<213> ORGANISM: artificial
<220> FEATURE:
<223> OTHER INFORMATION: melanoma antigen peptide 2

<400> SEQUENCE: 23

Arg Met Pro Pro Lys Pro Pro Leu Ala
1               5

<210> SEQ ID NO 24
<211> LENGTH: 9
<212> TYPE: PRT
<213> ORGANISM: artificial
<220> FEATURE:
<223> OTHER INFORMATION: melanoma antigen peptide 2

<400> SEQUENCE: 24
```

Arg Val Pro Pro Lys Pro Pro Leu Ala
1               5

<210> SEQ ID NO 25
<211> LENGTH: 9
<212> TYPE: PRT
<213> ORGANISM: artificial
<220> FEATURE:
<223> OTHER INFORMATION: melanoma antigen peptide 2

<400> SEQUENCE: 25

Arg Ile Pro Pro Lys Pro Pro Leu Ala
1               5

<210> SEQ ID NO 26
<211> LENGTH: 9
<212> TYPE: PRT
<213> ORGANISM: artificial
<220> FEATURE:
<223> OTHER INFORMATION: melanoma antigen peptide 2

<400> SEQUENCE: 26

Arg Gln Pro Pro Lys Pro Pro Leu Ala
1               5

<210> SEQ ID NO 27
<211> LENGTH: 9
<212> TYPE: PRT
<213> ORGANISM: artificial
<220> FEATURE:
<223> OTHER INFORMATION: melanoma antigen peptide 2

<400> SEQUENCE: 27

Arg Cys Pro Pro Lys Pro Pro Leu Val
1               5

<210> SEQ ID NO 28
<211> LENGTH: 9
<212> TYPE: PRT
<213> ORGANISM: artificial
<220> FEATURE:
<223> OTHER INFORMATION: melanoma antigen peptide 2

<400> SEQUENCE: 28

Arg Leu Pro Pro Lys Pro Pro Leu Val
1               5

<210> SEQ ID NO 29
<211> LENGTH: 9
<212> TYPE: PRT
<213> ORGANISM: artificial
<220> FEATURE:
<223> OTHER INFORMATION: melanoma antigen peptide 2

<400> SEQUENCE: 29

Arg Met Pro Pro Lys Pro Pro Leu Val
1               5

<210> SEQ ID NO 30
<211> LENGTH: 9
<212> TYPE: PRT
<213> ORGANISM: artificial
<220> FEATURE:
<223> OTHER INFORMATION: melanoma antigen peptide 2

<400> SEQUENCE: 30

Arg Val Pro Pro Lys Pro Pro Leu Val
1               5

```
<210> SEQ ID NO 31
<211> LENGTH: 9
<212> TYPE: PRT
<213> ORGANISM: artificial
<220> FEATURE:
<223> OTHER INFORMATION: melanoma antigen peptide 2

<400> SEQUENCE: 31

Arg Ile Pro Pro Lys Pro Pro Leu Val
1               5

<210> SEQ ID NO 32
<211> LENGTH: 9
<212> TYPE: PRT
<213> ORGANISM: artificial
<220> FEATURE:
<223> OTHER INFORMATION: melanoma antigen peptide 2

<400> SEQUENCE: 32

Arg Gln Pro Pro Lys Pro Pro Leu Val
1               5

<210> SEQ ID NO 33
<211> LENGTH: 9
<212> TYPE: PRT
<213> ORGANISM: artificial
<220> FEATURE:
<223> OTHER INFORMATION: melanoma antigen peptide 2

<400> SEQUENCE: 33

Arg Cys Pro Pro Lys Pro Pro Leu Leu
1               5

<210> SEQ ID NO 34
<211> LENGTH: 9
<212> TYPE: PRT
<213> ORGANISM: artificial
<220> FEATURE:
<223> OTHER INFORMATION: melanoma antigen peptide 2

<400> SEQUENCE: 34

Arg Leu Pro Pro Lys Pro Pro Leu Leu
1               5

<210> SEQ ID NO 35
<211> LENGTH: 9
<212> TYPE: PRT
<213> ORGANISM: artificial
<220> FEATURE:
<223> OTHER INFORMATION: melanoma antigen peptide 2

<400> SEQUENCE: 35

Arg Met Pro Pro Lys Pro Pro Leu Leu
1               5

<210> SEQ ID NO 36
<211> LENGTH: 9
<212> TYPE: PRT
<213> ORGANISM: artificial
<220> FEATURE:
<223> OTHER INFORMATION: melanoma antigen peptide 2

<400> SEQUENCE: 36

Arg Val Pro Pro Lys Pro Pro Leu Leu
1               5
```

```
<210> SEQ ID NO 37
<211> LENGTH: 9
<212> TYPE: PRT
<213> ORGANISM: artificial
<220> FEATURE:
<223> OTHER INFORMATION: melanoma antigen peptide 2

<400> SEQUENCE: 37

Arg Ile Pro Pro Lys Pro Pro Leu Leu
1               5

<210> SEQ ID NO 38
<211> LENGTH: 9
<212> TYPE: PRT
<213> ORGANISM: artificial
<220> FEATURE:
<223> OTHER INFORMATION: melanoma antigen peptide 2

<400> SEQUENCE: 38

Arg Gln Pro Pro Lys Pro Pro Leu Leu
1               5

<210> SEQ ID NO 39
<211> LENGTH: 9
<212> TYPE: PRT
<213> ORGANISM: artificial
<220> FEATURE:
<223> OTHER INFORMATION: MART-1 peptide

<400> SEQUENCE: 39

Ala Ala Gly Ile Gly Ile Leu Thr Val
1               5

<210> SEQ ID NO 40
<211> LENGTH: 10
<212> TYPE: PRT
<213> ORGANISM: artificial
<220> FEATURE:
<223> OTHER INFORMATION: MART-1 peptide

<400> SEQUENCE: 40

Glu Ala Ala Gly Ile Gly Ile Leu Thr Val
1               5                   10

<210> SEQ ID NO 41
<211> LENGTH: 10
<212> TYPE: PRT
<213> ORGANISM: artificial
<220> FEATURE:
<223> OTHER INFORMATION: MART-1 peptide

<400> SEQUENCE: 41

Ala Ala Gly Ile Gly Ile Leu Thr Val Ile
1               5                   10

<210> SEQ ID NO 42
<211> LENGTH: 10
<212> TYPE: PRT
<213> ORGANISM: artificial
<220> FEATURE:
<223> OTHER INFORMATION: MART-1 peptide

<400> SEQUENCE: 42

Glu Leu Ala Gly Ile Gly Ile Leu Thr Val
1               5                   10
```

MELANOMA ANTIGEN PEPTIDE AND USES THEREOF

The present application is filed pursuant to 35 U.S.C. 371 as a U.S. National Phase application of International Patent Application No. PCT/EP09/61354, which was filed Sep. 2, 2009, claiming the benefit of priority to European Patent Application No. 08305517.8, which was filed on Sep. 2, 2008. The entire text of the aforementioned applications is incorporated herein by reference in its entirety.

FIELD OF THE INVENTION

The invention relates to melanoma antigen peptides named MELOE and their use for preventing, treating and diagnosing melanoma.

BACKGROUND OF THE INVENTION

Melanomas are aggressive, frequently metastatic tumors derived from either melanocytes or melanocyte related nevus cells. Melanomas represent approximately three percent of all skin cancers and even when it is apparently localized to the skin, up to 30% of the patients will develop systemic metastasis. Classic modalities of treating melanoma include surgery, radiation and chemotherapy. Then immunotherapy and gene therapy have emerged as promising methods for treating melanoma. Rosenberg's results showed that adoptive transfer into patients with metastatic melanoma of tumor infiltrating lymphocytes (TIL) that recognize cancer antigens, are able to mediate the regression of metastatic cancer in 35 to 40% of melanoma patients.

In the last twenty years, many human melanoma antigens recognized by T cells have been identified using various methods such as cDNA cloning, MHC-bound peptide purification or T cell induction against candidate peptides or proteins. These antigens have been classified in several groups: melanocytic differentiation antigens (such as Melan-A/MART-1) (1), cancer-germline antigens, shared by several tumors and male germline cells (such as MAGE antigens) (2, 3), mutated antigens generated by genetic alterations (such as CDK4) (4), antigens overexpressed in various tumor types (such as PRAME) (5), and antigens aberrantly expressed in tumors (such as NA17-A and NA88-A) (6, 7). However, despite their high number, the immunogenicity of these antigens has not been elucidated yet, with the exception of Melan-A/MART-1. Indeed, the immunogenicity of the Melan-A antigen in melanoma has been strongly suggested by the analysis of several active (8, 9) and passive (10-15) immunotherapy protocols targeting this antigen.

The identification of additional melanoma antigens with a documented immunogenic potential remains a major issue to address for cancer immunotherapy, especially for melanoma.

SUMMARY OF THE INVENTION

One object of the invention is a melanoma antigen peptide comprising the amino acids motif:

TX$_2$NDECWPX$_9$ (SEQ ID NO: 2)

wherein X$_2$ is leucine, methionine, valine, isoleucine or glutamine and X$_9$ is alanine, valine or leucine, or

RX$_2$PPKPPLX$_9$ (SEQ ID NO: 3)

wherein X$_2$ is cysteine, leucine, methionine, valine, isoleucine or glutamine and X$_9$ is alanine, valine or leucine.

Another object of the invention is an expression vector comprising a nucleic acid sequence encoding the melanoma antigen peptide of the invention.

Another object of the invention is a host cell comprising said expression vector.

Another object of the invention is an antibody or fragment thereof that binds to MELOE-1 or MELOE-2.

Another object of the invention is a MHC/peptide multimer comprising a melanoma antigen peptide of the invention.

Another object of the invention is an immunising composition comprising
(a) at least one melanoma antigen peptide of the invention or
(b) at least one expression vector of the invention, or
(c) at least one host cell of the invention, or
(d) at least one antibody of the invention, or
(e) at least one nucleic acid sequence that encodes at least one melanoma antigen peptide of the invention.

Another object of the invention is a T lymphocyte that recognizes specifically a melanoma antigen peptide of the invention.

Another object of the invention is a composition for adoptive therapy comprising said T lymphocytes.

Another object of the invention is a method for producing said T lymphocytes comprising the steps of:
(a) stimulating PBMCs or TIL obtained from a subject with at least one melanoma antigen peptide of the invention,
(b) enriching the population of T lymphocytes specific for the melanoma antigen peptide(s) used in (a),
(c) optionally cloning said population of T lymphocytes specific for the melanoma antigen peptide(s) used in (a).

Another object of the invention is said immunising composition for preventing or treating melanoma in a subject in need thereof.

Another object of the invention is an in vitro method for diagnosing a melanoma in a subject in need thereof, comprising detecting the expression of at least one of:
MELOE mRNA (SEQ ID NO: 1),
MELOE-1 polypeptide (SEQ ID NO: 4),
MELOE-2 polypeptide (SEQ ID NO: 5),
in a sample obtained from said subject.

Another object of the invention is a method for monitoring a melanoma in a subject in need thereof, comprising determining the frequency of T lymphocytes that recognize specifically a melanoma antigen peptide of the invention

DETAILED DESCRIPTION OF THE INVENTION

Definitions

As used herein, the term "peptide" refers to an amino acid sequence having less than 50 amino acids. As used herein, the term "peptide" encompasses amino acid sequences having less than 50 amino acids, less than 40 amino acids, less than 30 amino acids, less than 25 amino acids, less than 20 amino acids, less than 15 amino acids or less than 10 amino acids.

As used herein, the term "antibody" refers to a protein capable of specifically binding an antigen, typically and preferably by binding an epitope or antigenic determinant or said antigen. The term "antibody" also includes recombinant proteins comprising the binding domains, as well as variants and fragments of antibodies. Examples of fragments of antibodies include Fv, Fab, Fab', F(ab')2, dsFv, scFv, sc(Fv)2, diabodies and multispecific antibodies formed from antibody fragments.

"Function-conservative variants" as used herein refer to those in which a given amino acid residue in a protein or enzyme has been changed (inserted, deleted or substituted) without altering the overall conformation and function of the polypeptide. Such variants include protein having amino acid alterations such as deletions, insertions and/or substitutions. A "deletion" refers to the absence of one or more amino acids in the protein. An "insertion" refers to the addition of one or more of amino acids in the protein. A "substitution" refers to the replacement of one or more amino acids by another amino acid residue in the protein. Typically, a given amino acid is replaced by an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

The term "Major Histocompatibility Complex" (MHC) is a generic designation meant to encompass the histo-compatibility antigen systems described in different species including the human leucocyte antigens (HLA).

The term "melanoma" as used herein includes, but is not limited to, melanomas, metastatic melanomas, melanomas derived from either melanocytes or melanocytes related nevus cells, melanocarcinomas, melanoepitheliomas, melanosarcomas, melanoma in situ, superficial spreading melanoma, nodular melanoma, lentigo maligna melanoma, acral lentiginous melanoma, ocular melanoma invasive melanoma or familial atypical mole and melanoma (FAM-M) syndrome. Such melanomas in mammals may be caused by, chromosomal abnormalities, degenerative growth and developmental disorders, mitogenic agents, ultraviolet radiation (UV), viral infections, inappropriate tissue expression of a gene, alterations in expression of a gene, or carcinogenic agents.

The term "treating" a disorder or a condition refers to reversing, alleviating or inhibiting the process of one or more symptoms of such disorder or condition. The term "preventing" a disorder or condition refers to preventing one or more symptoms of such disorder or condition.

The term "diagnosing" as used herein refers to the process of identifying a medical condition or disease. As used herein, the term "marker" or "biomarker" refers to a molecule used as a target for analysing subject's biological samples.

A "biological sample" as used herein refers to a variety of sample types obtained from a subject and can be used in a diagnostic or monitoring assay. Biological samples include but are not limited to blood, serum, plasma, ascitis, effusions, solid tissue samples such as a biopsy specimen or tissue cultures or cells derived there from, and the progeny thereof, clinical samples, cells in culture, cell supernatants, cell lysates. For example, biological samples include cells obtained from a tissue sample collected from a subject suspected of having a melanoma.

As used herein, the term "subject" denotes a mammal, such as a rodent, a feline, a canine, and a primate. Preferably a subject according to the invention is a human.

A "therapeutically effective amount" as used herein is intended for a minimal amount of active agent which is necessary to impart therapeutic benefit to a subject. For example, a "therapeutically effective amount of the active agent" to a subject is an amount of the active agent that induces, ameliorates or causes an improvement in the pathological symptoms, disease progression, or physical conditions associated with the disease affecting the subject.

The term "adjuvant" as used herein refers to a compound or a mixture that may be non-immunogenic when administered in the host alone, but that augments the host's immune response to an antigen when administered conjointly with that antigen.

The Invention

In order to identify new melanoma antigens, the inventors studied TIL populations that had been infused to melanoma patients in an adjuvant setting, after invaded lymph node excision, between 1994 and 2002, and who are still relapse-free (16). The authors previously showed a correlation between the infusion of melanoma specific TIL and relapse prevention (17). More recently, they showed a correlation between the infusion of Melan-A/MART-1 specific TIL and relapse prevention of HLA-A2 treated patient (14).

Nonetheless, in a number of TIL populations infused to relapse-free patients, a significant fraction of tumor-specific TIL remains of unknown specificity. In order to fully characterize these tumor specific TIL and to look for new tumor antigen(s) involved in relapse prevention, the inventors used a TIL population infused to M170 patient in 1998, who is still relapse-free today (18). This HLA-A2 TIL population contained a significant fraction of melanoma reactive TIL, among which Melan-A/A2 specific lymphocytes and lymphocytes of unknown specificity were present.

The study of these lymphocytes of unknown specificity led the inventors to identify a new mRNA sequence (SEQ ID NO: 1) named meloe (melanoma-overexpressed) that is overexpressed in melanoma, and that encodes polypeptides recognized by autologous TIL in the HLA-A2 context.

The invention provides a nucleic acid sequence SEQ ID NO: 1, which encodes two novel melanoma antigens peptides recognized by T cells: MELOE-1 and MELOE-2.

MELOE-1 is encoded by the open reading frame 1230-1370 bp of SEQ ID NO: 1 and

MELOE-2 is encoded by the open reading frame 285-404 bp of SEQ ID NO: 1.

The inventors identified two specific peptide motifs: TLNDECWPA in MELOE-1 and RCPPKPPLA in MELOE-2, said motifs being capable of binding to HLA-A2 molecule and inducing a T cell response.

Concerning the peptide motifs capable of binding to HLA-A2, it is known in the art that the $2^{nd}$ amino acid from the N-terminus can be leucine, methionine, valine, isoleucine or glutamine and the amino acid at C-terminus can be leucine or valine (39,40).

Therefore, one object of the invention is a melanoma antigen peptide comprising the amino acids motif:

(a) TX$_2$NDECWPX$_9$ (SEQ ID NO: 2)

wherein X$_2$ is leucine, methionine, valine, isoleucine or glutamine and X$_9$ is alanine, valine or leucine, or (b) RX$_2$PPKPPLX$_9$ (SEQ ID NO: 3)

wherein X$_2$ is cysteine, leucine, methionine, valine, isoleucine or glutamine and X$_9$ is alanine, valine or leucine.

In one embodiment of the invention, by "melanoma antigen peptide" is meant a peptide capable of binding to HLA molecule and causing a cellular or humoral response in a subject.

In a first embodiment of the invention, said melanoma antigen peptide may comprise a specific motif such that the polypeptide binds an HLA molecule and induces a CTL response.

In a second embodiment of the invention, said melanoma antigen peptide may comprise a specific motif such that the polypeptide binds an HLA molecule and induces a helper T cell response.

In one embodiment of the invention, said melanoma antigen peptides as described here above are HLA-A2 restricted.

In one embodiment of the invention, said melanoma antigen peptide is an amino acid sequence of less than 50 amino acids long that comprises the amino acid motif SEQ ID NO: 2 or SEQ ID NO: 3 as defined here above.

In another embodiment of the invention, said melanoma antigen peptide is an amino acid sequence of less than 45 amino acids long that comprises the amino acid motif SEQ ID NO: 2 or SEQ ID NO: 3 as defined here above.

In another embodiment of the invention, said melanoma antigen peptide is an amino acid sequence of less than 40 amino acids long that comprises the amino acid motif SEQ ID NO: 2 or SEQ ID NO: 3 as defined here above.

In another embodiment of the invention, said melanoma antigen peptide is an amino acid sequence of less than 30 amino acids long that comprises the amino acid motif SEQ ID NO: 2 or SEQ ID NO: 3 as defined here above.

In another embodiment of the invention, said melanoma antigen peptide is an amino acid sequence of less than 20 amino acids long that comprises the amino acid motif SEQ ID NO: 2 or SEQ ID NO: 3 as defined here above.

In another embodiment of the invention, said melanoma antigen peptide is an amino acid sequence of less than 15 amino acids long that comprises the amino acid motif SEQ ID NO: 2 or SEQ ID NO: 3 as defined here above.

In another embodiment of the invention, said melanoma antigen peptide is an amino acid sequence of 9, 10 or 11 amino acids long that comprises the amino acid motif SEQ ID NO: 2 or SEQ ID NO: 3 as defined here above.

In one embodiment of the invention, said melanoma antigen peptide is selected in the group consisting of MELOE-1 having the sequence SEQ ID NO: 4 and MELOE-2 having the sequence SEQ ID NO: 5.

SEQ ID NO: 4
MSCVGYPDEATSREQFLPSEGAACPPWHPSERISSTLNDECWPASL

SEQ ID NO: 5
MSENAGGAVARTATAFCALVSPTPQPRCPPKPPLAALCQ

In another embodiment of the invention, said melanoma antigen peptide is selected in the group consisting of MELOE-1 peptides having the sequence SEQ ID NO: 6 to SEQ ID NO: 20 and MELOE-2 peptides having the sequence SEQ ID NO: 21 to SEQ ID NO: 38.

| | | | |
|---|---|---|---|
| MELOE-1 SEQ ID NO 6 | X$_2$ = L | X$_9$ = A | TLNDECWPA |
| MELOE-1 SEQ ID NO 7 | X$_2$ = M | X$_9$ = A | TMNDECWPA |
| MELOE-1 SEQ ID NO 8 | X$_2$ = V | X$_9$ = A | TVNDECWPA |
| MELOE-1 SEQ ID NO 9 | X$_2$ = I | X$_9$ = A | TINDECWPA |
| MELOE-1 SEQ ID NO 10 | X$_2$ = Q | X$_9$ = A | TQNDECWPA |
| MELOE-1 SEQ ID NO 11 | X$_2$ = L | X$_9$ = V | TLNDECWPV |
| MELOE-1 SEQ ID NO 12 | X$_2$ = M | X$_9$ = V | TMNDECWPV |
| MELOE-1 SEQ ID NO 13 | X$_2$ = V | X$_9$ = V | TVNDECWPV |
| MELOE-1 SEQ ID NO 14 | X$_2$ = I | X$_9$ = V | TINDECWPV |
| MELOE-1 SEQ ID NO 15 | X$_2$ = Q | X$_9$ = V | TQNDECWPV |
| MELOE-1 SEQ ID NO 16 | X$_2$ = L | X$_9$ = L | TLNDECWPL |
| MELOE-1 SEQ ID NO 17 | X$_2$ = M | X$_9$ = L | TMNDECWPL |
| MELOE-1 SEQ ID NO 18 | X$_2$ = V | X$_9$ = L | TVNDECWPL |
| MELOE-1 SEQ ID NO 19 | X$_2$ = I | X$_9$ = L | TINDECWPL |
| MELOE-1 SEQ ID NO 20 | X$_2$ = Q | X$_9$ = L | TQNDECWPL |
| MELOE-2 SEQ ID NO 21 | X$_2$ = C | X$_9$ = A | RCPPKPPLA |
| MELOE-2 SEQ ID NO 22 | X$_2$ = L | X$_9$ = A | RLPPKPPLA |
| MELOE-2 SEQ ID NO 23 | X$_2$ = M | X$_9$ = A | RMPPKPPLA |
| MELOE-2 SEQ ID NO 24 | X$_2$ = V | X$_9$ = A | RVPPKPPLA |
| MELOE-2 SEQ ID NO 25 | X$_2$ = I | X$_9$ = A | RIPPKPPLA |
| MELOE-2 SEQ ID NO 26 | X$_2$ = Q | X$_9$ = A | RQPPKPPLA |
| MELOE-2 SEQ ID NO 27 | X$_2$ = C | X$_9$ = V | RCPPKPPLV |
| MELOE-2 SEQ ID NO 28 | X$_2$ = L | X$_9$ = V | RLPPKPPLV |
| MELOE-2 SEQ ID NO 29 | X$_2$ = M | X$_9$ = V | RMPPKPPLV |
| MELOE-2 SEQ ID NO 30 | X$_2$ = V | X$_9$ = V | RVPPKPPLV |
| MELOE-2 SEQ ID NO 31 | X$_2$ = I | X$_9$ = V | RIPPKPPLV |
| MELOE-2 SEQ ID NO 32 | X$_2$ = Q | X$_9$ = V | RQPPKPPLV |
| MELOE-2 SEQ ID NO 33 | X$_2$ = C | X$_9$ = L | RCPPKPPLL |
| MELOE-2 SEQ ID NO 34 | X$_2$ = L | X$_9$ = L | RLPPKPPLL |
| MELOE-2 SEQ ID NO 35 | X$_2$ = M | X$_9$ = L | RMPPKPPLL |
| MELOE-2 SEQ ID NO 36 | X$_2$ = V | X$_9$ = L | RVPPKPPLL |
| MELOE-2 SEQ ID NO 37 | X$_2$ = I | X$_9$ = L | RIPPKPPLL |
| MELOE-2 SEQ ID NO 38 | X$_2$ = Q | X$_9$ = L | RQPPKPPLL |

The invention also encompasses peptides that are function-conservative variants of melanoma antigen peptides comprising SEQ ID NO: 2 or SEQ ID NO: 3 as described here above.

Typically, the invention encompasses peptides substantially identical to melanoma antigen peptides comprising SEQ ID NO: 2 or SEQ ID NO: 3 in which one or more residues have been conservatively substituted with a functionally similar residue and which displays the functional aspects of the melanoma antigen peptides comprising SEQ ID NO: 2 and SEQ ID NO: 3 as described here above, i.e. being still able to bind to an HLA molecule in substantially the same way as a peptide consisting of the given amino acid sequence.

Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The term "conservative substitution" also includes the use of a chemically derivatized residue in place of a non-derivatized residue. "Chemical derivative" refers to a subject peptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Chemical derivatives also include peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

In one embodiment of the invention, the melanoma antigen peptide consists essentially of an amino acid sequence according to SEQ ID NO: 6 to 38 or a variant thereof.

According to the invention, "consisting essentially of" shall mean that a peptide according to the present invention, in addition to the sequence according to any of SEQ ID No. 6 to SEQ ID No. 38 or a variant thereof, contains additional N- and/or C-terminally located stretches of amino acids that are not necessarily forming part of the peptide that functions as core sequence of the peptide comprising the binding motif and as an immunogenic epitope.

According to the invention, the melanoma antigen peptides of the invention can be obtained by synthesizing the peptides according to the method for peptide synthesis known in the art.

Another object of the invention is an expression vector comprising a nucleic acid sequence encoding an amino sequence comprising SEQ ID NO: 2 or SEQ ID NO: 3 as described here above.

In one embodiment of the invention, said expression vector comprises the nucleic acid sequence corresponding to the open reading frame 1230-1370 bp of SEQ ID NO: 1.

In another embodiment of the invention, said expression vector comprises the nucleic acid sequence corresponding to the open reading frame 285-404 bp of SEQ ID NO: 1.

In another embodiment of the invention, said expression vector comprises the nucleic acid sequence corresponding to the open reading frame 1230-1370 bp of SEQ ID NO: 1 combined to the nucleic acid sequence corresponding to the open reading frame 285-404 bp of SEQ ID NO: 1.

In another embodiment of the invention, said expression vector comprises a nucleic acid sequence encoding SEQ ID NO: 4 or SEQ ID NO: 5.

In another embodiment of the invention, said expression vector comprises a nucleic acid sequence encoding a polypeptide comprising at least one amino acid sequence selected from SEQ ID NO: 6 to SEQ ID NO: 38.

According to the invention, expression vectors suitable for use in the invention may comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus, lentivirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods or commercially available.

Another object of the invention is a host cell comprising an expression vector as described here above.

According to the invention, examples of host cells that may be used are eukaryote cells, such as animal, plant, insect and yeast cells and prokaryotes cells, such as *E. coli*. The means by which the vector carrying the gene may be introduced into the cells include, but are not limited to, microinjection, electroporation, transduction, or transfection using DEAE-dextran, lipofection, calcium phosphate or other procedures known to one skilled in the art.

In a preferred embodiment, eukaryotic expression vectors that function in eukaryotic cells are used. Examples of such vectors include, but are not limited to, viral vectors such as retrovirus, adenovirus, adeno-associated virus, herpes virus, vaccinia virus, poxvirus, poliovirus; lentivirus, bacterial expression vectors, plasmids, such as pcDNA3 or the baculovirus transfer vectors. Preferred eukaryotic cell lines include, but are not limited to, COS cells, CHO cells, HeLa cells, NIH/3T3 cells, 293 cells (ATCC #CRL1573), T2 cells, dendritic cells, or monocytes.

In one embodiment of the invention, said antibody or fragment thereof binds to MELOE-1 (SEQ ID NO: 4).

In another embodiment of the invention, said antibody or fragment thereof binds MELOE-2 (SEQ ID NO: 5).

In one embodiment of the invention, said antibody is monoclonal. In another embodiment of the invention, said antibody is polyclonal.

Such antibodies may be easily prepared, for example, according to the method described in "Antibodies: A laboratory manual", Lane H. D. et al. eds, Cold Spring Harbor Laboratory Press, New York, 1989 or Antibody Engineering: Methods and Protocols, 2003, Benny K. Lo.

Another object of the invention is a MHC/peptide multimer comprising a melanoma antigen peptide (SEQ ID NO: 6 to 38) as described here above. According to the invention, said MHC/peptide multimer include, but are not limited to, a MHC/peptide dimer, trimer, tetramer or pentamer.

In one embodiment of the invention, said MHC/peptide multimer is a HLA-A2/peptide multimer.

Methods for obtaining MHC/peptide tetramers are described in WO96/26962 and WO01/18053, which are incorporated by reference.

In one embodiment of the invention, said MHC/peptide multimer can be used to visualise T cell populations that are specific for the complex HLA-A2/melanoma antigen peptide as described here above.

In another embodiment of the invention, said MHC/peptide multimer can be used for the detection and/or isolation by screening (in flow cytometry or by immunomagnetic screening) of T cell population that are specific for a complex HLA/melanoma antigen peptide as described here above.

In another embodiment of the invention, said HLA-A2/peptide multimer can be used for the detection and/or isolation by screening (in flow cytometry or by immunomagnetic screening) of T cell population that are specific for a complex HLA-A2/melanoma antigen peptide as described here above.

Another object of the invention is beads coated with MHC/peptide multimers as described here above.

Another object of the invention is an immunising composition comprising
(a) at least one melanoma antigen peptide as described here above or
(b) at least one expression vector as described here above, or
(c) at least one host cell as described here above, or
(d) at least one antibody as described here above, or
(e) at least one nucleic acid sequence that encodes at least one melanoma antigen peptide as described here above.

In one embodiment, said immunising composition comprises the melanoma antigen peptide MELOE-1 having the sequence SEQ ID NO: 4 or the melanoma antigen peptide MELOE-2 having the sequence SEQ ID NO: 5.

In another embodiment of the invention, said immunising composition comprises at least one melanoma antigen peptide selected in the group consisting of SEQ ID NO: 6 to SEQ ID NO: 38.

The prophylactic administration of the immunising composition of the invention should serve to prevent or attenuate melanoma in a mammal. In a preferred embodiment mammals, preferably human, at high risk for melanoma are prophylactically treated with the immunising composition of the invention. Examples of such mammals include, but are not limited to, humans with a family history of melanoma, humans with a history of atypical moles, humans with a history of FAM-M syndrome or humans afflicted with melanoma previously resected and therefore at risk for reoccurrence.

When provided therapeutically, the immunising composition of the invention is provided to enhance the patient's own immune response to the melanoma antigen present on the melanoma or metastatic melanoma.

In one embodiment of the invention, the peptides of the invention may be conjugated with lipoprotein or administered in liposomal form or with adjuvant.

In one embodiment, said immunising composition is a pharmaceutical composition.

In such embodiment, said immunising composition, for human use, comprises at least one melanoma antigen peptide as described here above or at least one antibody as described here above, together with one or more pharmaceutically acceptable carriers and, optionally, other therapeutic ingredients. The carrier(s) must be "acceptable" in the sense of being compatible with the other ingredients of the composition and not deleterious to the recipient thereof. The immunising compositions may conveniently be presented in unit dosage form and may be prepared by any method well-known in the pharmaceutical art.

Immunising compositions suitable for intravenous, intradermal, intramuscular, subcutaneous, or intraperitoneal administration conveniently comprise sterile aqueous solutions of the active agent with solutions which are preferably isotonic with the blood of the recipient. Such compositions may be conveniently prepared by dissolving solid active ingredient in water containing physiologically compatible substances such as sodium chloride (e.g. 0.1-2.0M), glycine, and the like, and having a buffered pH compatible with physiological conditions to produce an aqueous solution, and rendering said solution sterile. These may be present in unit or multi-dose containers, for example, sealed ampoules or vials.

The immunising compositions of the invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11-10,000 parts by weight per part by weight of active agent. If two or more stabilizers are to be used, their total amount is preferably within the range specified above. These stabilizers are used in aqueous solutions at the appropriate concentration and pH. The specific osmotic pressure of such aqueous solutions is generally in the range of 0.1-3.0 osmoles, preferably in the range of 0.8-1.2. The pH of the aqueous solution is adjusted to be within the range of 5.0-9.0, preferably within the range of 6-8.

Additional pharmaceutical methods may be employed to control the duration of action. Controlled release preparations may be achieved through the use of polymer to complex or absorb the peptides of the invention. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the melanoma antigen peptides of the invention into particles of a polymeric material such as polyesters, polyamino acids, hydrogels, poly(lactic acid) or ethylene vinylaceiate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

Immunisation of a subject with the immunising composition of the invention can be conducted by conventional methods, for example, in the presence of conventional adjuvants. Examples of conventional adjuvant include, but are not limited to, metal salts, oil in water emulsions, Toll like receptors agonists, saponins, lipid A, alkyl glucosaminide phosphate, Freund's adjuvant, keyhole limpet haemocyanin (KLH), mannan, BCG, alum, cytokines such as IL-1, IL-2, macrophage colony stimulating factor, and tumor necrosis factor; and (6) other substances that act as immunostimulating agents such as muramyl peptides or bacterial cell wall components, toxins, toxoids and TLR ligands.

The immunising composition can be administered by any route appropriate for antibody production and/or T cell activation such as intravenous, intraperitoneal, intramuscular, subcutaneous, and the like. The immunising composition may be administered once or at periodic intervals until a significant titer of anti-MELOE-1 or MELOE-2 immune cells or anti-MELOE-1 or MELOE-2 antibody is produced. The presence of anti-MELOE-1 or MELOE-2 immune cells may be assessed by measuring the frequency of precursor CTL (cytoxic T-lymphocytes) against the melanoma antigen peptides of the invention prior to and after immunization by specific tetramer labelling (13) or by a CTL precursor analysis assay (41). The antibody may be detected in the serum using an immunoassay.

Antibodies directed to the melanoma antigens of the invention can also be used directly as anti-melanoma agents. To prepare antibodies, a host animal may be immunized using the MELOE-1 (SEQ ID NO: 4) or MELOE-2 (SEQ ID NO: 4) protein or others melanoma antigen peptides as described here above. The host serum or plasma is collected following an appropriate time to provide a composition comprising antibodies reactive to said melanoma antigen peptides. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-cancer agents such as chemotherapy.

The immunising composition of the invention comprising antibodies as described here above can be made even more compatible with the host system by minimizing potential adverse immune system responses. This is accomplished by removing all or a portion of the Fc portion of a foreign species antibody or using an antibody of the same species as the host subject, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, nonhuman mammal-human chimeras, rodent-human chimeras, murine-human and rat-human chimeras.

Methods for obtaining said antibodies, chimeric antibodies and humanized chimeric antibodies are well-known in the art.

The immunising composition comprising the antibodies of the invention can also be used as a means of enhancing the immune response. The antibodies can be administered in amounts similar to those used for other therapeutic administrations of antibody. For example, pooled gamma globulin is administered at a range of about 1 mg to about 100 mg per subject. Thus, antibodies reactive with the melanoma antigen peptides of the invention can be passively administered alone or in conjunction with other anti-cancer therapies to a mammal afflicted with melanoma. Examples of anti-cancer therapies include, but are not limited to, chemotherapy, radiation therapy, adoptive immunotherapy therapy with TIL.

The antibodies or chimeric antibodies described herein may also be coupled to toxin molecules, radioisotopes and drugs by conventional methods. Examples of toxins to which the antibodies may be coupled to include, but are not limited to, ricin or diphtheria toxin. Examples of drugs or chemotherapeutic agents include, but are not limited to, cyclophosphamide or doxorubicin. Examples of radioisotopes, include, but are not limited to, $^{131}$I. Antibodies covalently conjugated to the aforementioned agents can be used in cancer immunotherapy for treating melanoma.

If the subject to be immunized is already afflicted with melanoma or metastatic melanoma, the immunising composition of the invention can be administered in conjunction with other therapeutic treatments. Examples of other therapeutic treatments includes, but are not limited to, adoptive T cell immunotherapy, coadministration of cytokines or other therapeutic drugs for melanoma.

In one embodiment of the invention, said immunising composition comprising
 (a) at least one melanoma antigen peptide as described here above or
 (b) at least one expression vector as described here above, or
 (c) at least one host cell as described here above, or
 (d) at least one antibody as described here above, or
 (e) at least one nucleic acid encoding at least one melanoma antigen peptide of the invention,
may further comprise
(a') at least one MART-1 or Melan-A peptide as described in EP1630229, or
(b') at least one expression vector comprising a nucleic acid encoding a MART-1 peptide, or
(c') at least one host cell comprising the expression vector of (b'), or
(d') at least one antibody or fragment thereof that recognizes specifically a MART-1 peptide, or
(e') at least one nucleic acid encoding a MART-1 peptide.

Examples of MART-1 peptides include, but are not limited to, AAGIGILTV (SEQ ID NO: 39), EAAGIGILTV (SEQ ID NO: 40), AAGIGILTVI (SEQ ID NO: 41), ELAGIGILTV (SEQ ID NO: 42).

The dose of melanoma antigen peptides of the invention or MART-1 peptides to be administered to a subject may be adjusted as appropriate depending on, for example, the disease to be treated, the age and the body weight of said subject. Ranges of melanoma antigen peptides of the invention or MART-1 peptides that may be administered are about 0.001 to about 100 mg per subject, preferred doses are about 0.01 to about 10 mg per subject.

The immunising composition of the invention may be evaluated first in animal models, initially rodents, and in nonhuman primates and finally in humans. The safety of the immunization procedures is determined by looking for the effect of immunization on the general health of the immunized animal (weight change, fever, appetite behavior etc.) and looking for pathological changes on autopsies. After initial testing in animals, melanoma cancer patients can be tested. Conventional methods would be used to evaluate the immune response of the patient to determine the efficiency of the immunising composition.

Another object of the invention is an antigen presenting cell comprising a complex HLA antigen and a melanoma antigen peptide of the invention.

In one embodiment of the invention, said complex HLA antigen is a HLA-A2 antigen.

In one embodiment of the invention, said antigen presenting cell is derived from the subject to be treated.

The term "antigen presenting cell" (APCs) refers to any cell that expresses an HLA antigen capable of presenting the melanoma antigen peptide of the invention on its surface. Dendritic cells, which are reported to have an especially high antigen-presenting ability, are preferred. In another embodiment, artificial APCs may also be used such mammalian cells (fibroblast, endothelial cells, keratinocytes), insect cells, or cell lines.

In order to prepare such APCs of the invention, cells having an antigen-presenting ability are isolated from the subject to be treated, and pulsed ex vivo with at least one melanoma antigen peptide of the invention to form a complex with the HLA-A2 antigen.

In case dendritic cells are used, the APC of the invention can be prepared as follows. Lymphocytes are isolated from peripheral blood of the subject to be treated by Ficoll method; adherent cells are separated from non-adherent cells; the adherent cells are then cultured in the presence of GM-CSF and IL-4 to induce dendritic cells; and the dendritic cells are pulsed by culturing with at least one melanoma antigen peptide of the invention to obtain the APCs of the invention. The dendritic cells should be exposed to the melanoma antigen peptide for sufficient time to allow the antigens to be internalized and presented on the dendritic cells surface. The resulting dendritic cells can then be re-administrated to the subject to be treated. Such methods are described in WO93/208185 and EP0563485, which are incorporated by reference.

Another object of the invention is a composition for active immunotherapy comprising antigen presenting cells comprising a complex HLA antigen and a melanoma antigen peptide of the invention.

In one embodiment of the invention, said antigen presenting cells comprise a complex HLA-A2 antigen and a melanoma antigen peptide of the invention.

Said APCs may be preferably contained in physiological saline, phosphate buffered saline (PBS), culture medium, or the like. Administration may be achieved, for example, intravenously, hypodermically, or intradermally.

By returning the above described composition for active immunotherapy into the subject's body, specific CTL may be efficiently induced in the patient who is positive for meloe, and thereby tumor can be treated.

Another object of the invention is a T lymphocyte that recognizes specifically the melanoma antigen peptide of the invention.

In one embodiment of the invention, said T lymphocyte is a cytotoxic T lymphocyte.

In another embodiment of the invention, said T lymphocyte is HLA-A2 restricted.

In another embodiment of the invention, said T lymphocyte is a T cell clone.

In another embodiment, said T lymphocyte is a genetically modified T lymphocyte that expresses a TCR that recognizes specifically the melanoma antigen peptide of the invention.

Another object of the invention is a composition for adoptive therapy comprising said T lymphocytes as described here above that recognizes specifically the melanoma antigen peptide of the invention.

In the case of melanoma, it has been observed that an adoptive immunotherapy wherein intratumoral T cell infiltrate taken from the subject to be treated are cultured ex vivo in large quantities, and then returned into the patient achieves a therapeutic gain.

It is preferred that the T cells are contained in physiological saline, phosphate buffered saline (PBS), culture medium, or the like in order to their stable maintain. Administration may be achieved, for example, intravenously or intra-tumoraly. By returning the T cells that recognizes specifically the melanoma antigen peptide of the invention into the subject's body, the toxicity of said T cells on tumor cells is enhanced in the patient who is positive for meloe. The tumor cells are destroyed and thereby the treatment of tumor is achieved.

Examples of where T-lymphocytes can be isolated, include but are not limited to, peripheral blood cells lymphocytes (PBL), lymph nodes, or tumor infiltrating lymphocytes (TIL).

Such lymphocytes can be isolated from tumor or peripheral blood of the individual to be treated by methods known in the art and cultured in vitro. Lymphocytes are cultured in media such as RPMI or RPMI 1640 for 2-5 weeks, preferably for 2-3 weeks. Viability is assessed by trypan blue dye exclusion assay. The lymphocytes are exposed to the melanoma antigen peptide of the invention for all of the culture duration.

In a preferred embodiment the lymphocytes are exposed to the melanoma antigen peptide of the invention at a concentration of about 1 to about 10 micrograms($\mu$g)/ml per $10^7$ cells for all the duration of lymphocyte culture. Cytokines may be added to the lymphocyte culture such as IL-2.

The melanoma antigen peptide of the invention may be added to the culture in presence of antigen presenting cells such as dendritic cells or allogeneic irradiated melanoma cell line cells.

After being sensitized to the peptide, the T-lymphocytes are administered to the subject in need of such treatment.

Examples of how these sensitized T-cells can be administered to the mammal include but are not limited to, intravenously, intraperitoneally or intralesionally. Parameters that may be assessed to determine the efficacy of these sensitized T-lymphocytes include, but are not limited to, production of immune cells in the subject being treated or tumor regression. Conventional methods are used to assess these parameters. Such treatment can be given in conjunction with cytokines or gene modified cells (Rosenberg, S. A. et al. (1992) Human Gene Therapy, 3: 75-90; Rosenberg, S. A. et al. (1992) Human Gene Therapy, 3: 57-73).

Another object of the invention is a composition for adoptive therapy comprising HLA-A2 restricted T lymphocytes that recognizes specifically the melanoma antigen peptide of the invention, which further comprises HLA-A2 restricted T lymphocytes that recognize specifically a MART-1/Melan-A peptide.

HLA-A2 restricted T lymphocytes that recognize specifically a MART-1/Melan-A peptide are known in the art and were described in Vignard et al., 2005.

Another object of the invention is a method for producing T lymphocytes that recognize specifically a melanoma antigen peptide of the invention, said method comprising the steps of:
(a) stimulating PBMCs or tumor infiltrating lymphocytes (TIL) obtained from a subject with at least one melanoma antigen peptide of the invention,
(b) enriching the population of T lymphocytes specific for the melanoma antigen peptide(s) used in (a),
(c) optionally cloning said population of T lymphocytes specific for the melanoma antigen peptide(s) used in (a).

Enrichment and/or cloning may be carried out by using an MHC/peptide multimer as described here above. Cloning may also be carried out by conventional methods.

In one embodiment of the invention, the T lymphocytes that recognize specifically a melanoma antigen peptide of the invention are HLA-A2 restricted. In such embodiment, enrichment and/or cloning may be carried out by using an HLA-A2/peptide multimer as described here above.

Stimulation of PBMCs may be carried out with at least one melanoma antigen peptide of the invention alone, or presented by an antigen presenting cell such as dendritic cells or allogeneic irradiated melanoma cell line cells. Typically, cytokines such as IL-2 may also be added to the culture.

Another object of the invention is a composition for adoptive therapy that comprises lymphocytes that recognizes specifically the melanoma antigen peptide of the invention for preventing or treating melanoma in a subject in need thereof, wherein said T lymphocytes are to be re-administrated to the subject.

In one embodiment, said lymphocytes that recognize specifically the melanoma antigen peptide of the invention are HLA-A2 restricted.

Another object of the invention is an immunising composition comprising
(a) at least one melanoma antigen peptide as described here above or
(b) an expression vector comprising a nucleic acid sequence encoding a melanoma antigen peptide defined in (a) as described here above, or
(c) a host cell comprising an expression vector defined in (b) as described here above, or
(d) an antibody that recognizes specifically a melanoma antigen peptide defined in (a) as described here above, or
(e) at least one nucleic acid encoding at least one melanoma antigen peptide of the invention,
for preventing or treating melanoma in a subject in need thereof.

Another object of the invention is a composition for immunotherapy that comprises antigen presenting cells comprising a HLA molecule and a melanoma antigen peptide of the invention.

In one embodiment, said complex HLA/peptide is a complex HLA-A2/melanoma antigen peptide of the invention.

The invention also relates to a method for treating melanoma in a subject in need thereof, comprising administering a therapeutically effective amount of
(a) at least one melanoma antigen peptide as described here above or
(b) an expression vector as described here above, or
(c) a host cell as described here above, or
(d) an antibody as described here above, or
(e) at least one nucleic acid encoding at least one melanoma antigen peptide of the invention.

The invention also relates to a method for treating melanoma in a subject in need thereof, comprising administering a therapeutically effective amount of T lymphocytes that recognizes specifically the melanoma antigen peptide of the invention. In one embodiment, said T lymphocytes are HLA-A2 restricted.

The invention also relates to a method for treating melanoma in a subject in need thereof, comprising administering a therapeutically effective amount of antigen presenting cells comprising a complex HLA antigen and a melanoma antigen peptide of the invention. In one embodiment, said complex HLA/peptide is a complex HLA-A2/melanoma antigen peptide of the invention.

The inventors observed that meloe cDNA expression level was higher in melanomas than in melanocytes and that meloe expression was very low in other tumor cell lines such as breast or lung tumor cell lines.

Therefore, one object of the invention is meloe as a biomarker of melanoma.

Another object of the invention is an in vitro method for diagnosing a melanoma in a subject in need thereof, comprising detecting the expression of at least one of:
meloe mRNA (SEQ ID NO: 1),
MELOE-1 peptide (SEQ ID NO: 4),
MELOE-2 peptide (SEQ ID NO: 5),
in a sample obtained from said subject.

Examples of methods for determining the transcription level of meloe cDNA include, but are not limited to Northern blotting, RNase protection, polymerase chain reaction (PCR), quantitative PCR, real-time PCR.

Meloe mRNA and MELOE-1 and MELOE-2 proteins are present in melanoma cells. It is therefore an aspect of the invention to provide meloe nucleic acid probes to be utilized in detecting meloe RNA or MELOE-1 or MELOE-2 proteins or alterations in the level of meloe mRNA or MELOE-1 or MELOE-2 proteins in biological sample isolated from a subject afflicted with melanomas. By alterations in the level of meloe mRNA or MELOE-1 or MELOE-2 proteins, we mean an increase or decrease in the level of a RNA or MELOE-1 or MELOE-2 proteins relative to a control sample or the appearance or disappearance of the meloe mRNA or MELOE-1 or MELOE-2 proteins relative to a control sample. Detection in the alterations of meloe mRNA or MELOE-1 or MELOE-2 proteins will allow for diagnosis or the assessment of the diseased state. Therefore, alterations in the level of meloe mRNA or MELOE-1 or MELOE-2 proteins may be predictive of the prognosis for the afflicted mammal.

In another embodiment, the meloe nucleic acid of this invention can be used in in situ hybridization on mammalian tissues to determine the precise site or subcellular site of expression of the meloe gene within a tissue. A preferred method of labelling the meloe nucleic acid sequence is synthesizing a $^{35}$S-labeled RNA probe by in vitro transcription utilizing SP6 polymerase. Conventional methods for preparation of tissues for in situ, synthesis of probes and detection of signal are known in the art. The probe is then contacted with mammalian tissue sections and in situ analyses performed by conventional methods. Examples of tissues that can be used include, but are not limited to, mammalian embryos, adult mammalian tissues, such as skin, lymph nodes and retina, biopsy specimens, pathology specimens and necropsy specimens. In a preferred embodiment, meloe in situ probes may be used to evaluate meloe RNA expression in diseased tissue for invasive early melanoma to characterize radial and vertical growth phases of the melanoma lesion and assess the margins of the disease within the tissue.

In another embodiment of the invention, the antibodies of this invention may be used in immunoassays to detect the MELOE-1 or MELOE-2 protein in biological samples. In this method, the antibodies of the invention are contacted with a biological sample and the formation of a complex between the melanoma antigen peptide and antibody is detected. Immunoassays of the present invention may be radioimmunoassay, Western blot assay, immunofluorescent assay, enzyme immunoassay, chemiluminescent assay, immunohistochemical assay and the like. Standard techniques for ELISA are known in the art. Such assays may be direct, indirect, competitive, or noncompetitive immunoassays as described in the art. Biological samples appropriate for such detection assays include mammalian tissues, melanoma and melanocyte cell lines, skin, retina, lymph nodes, pathology specimens, necropsy specimens, and biopsy specimens. Proteins may be isolated from biological samples by conventional methods.

The antibodies of this invention can therefore be used in immunoassays to detect MELOE-1 or MELOE-2 proteins or alteration in the level of expression of these proteins in biological samples isolated from mammals afflicted with a disease or disorder. Examples of biological samples include, but are not limited to, mammalian tissues, biopsy tissue samples, melanoma and lymph node biopsy samples, pathology and tissue samples. Examples of diseases that can be assessed by these immunoassays, include, but are not limited to, melanomas and tissues which are secondary sites for melanoma metastasis. By alteration in level of expression, we mean an increase or decrease of the MELOE-1 or MELOE-2 protein or portions thereof relative to a control sample. The antibodies of this invention can therefore be used in an immunoassay to diagnose, assess or prognoses a mammal afflicted with melanoma.

In another embodiment of the invention, rabbit antisera containing antibodies which specifically recognize the melanoma antigen peptides of the invention may be used to detect said peptides in Western Blot Analysis. Using conventional methods, rabbits may be immunized with at least one melanoma antigen peptides of the invention conjugated to carriers. Preferably about 0.1 to about 10 mg of antigen in adjuvant may be used, most preferably about 1 mg of antigen in adjuvant may be used. The animal receives similar booster doses and antisera titer is assessed by ELISA assay. Satisfactory levels of antisera are obtained when the anti-peptide antibody titer reaches a plateau. This antibody can be used in the standard immunoassays described above.

Another object of the invention is a method for monitoring a melanoma in a subject in need thereof, comprising determining the frequency of T lymphocytes that recognize specifically a melanoma antigen peptide of the invention.

In one embodiment of the invention, said T lymphocytes are HLA-A2 restricted.

In one embodiment of the invention, the frequency of T lymphocytes that recognize specifically a melanoma antigen peptide of the invention may be determined by using an MHC/peptide multimer as described here above.

According to the invention, an increase in the frequency of T lymphocytes that recognize specifically a melanoma antigen peptide of the invention correlates with relapse prevention.

Another object of the invention is a kit comprising:
an antibody that recognizes specifically MELOE-1 or MELOE-2 and/or
primers or probes for meloe mRNA detection, and/or
an MHC/peptide multimer comprising a melanoma antigen peptide of the invention.

In one embodiment, said kit further comprises a solid support, wherein said solid support is selected from the group consisting of wells of reaction trays, test tubes, polystyrene beads, strips, membranes and microparticles.

In another embodiment, said kit further comprises a label, wherein said label is selected in the group consisting of enzymes, radioisotopes, fluorescent compounds and chemiluminescent compounds.

The following examples are given for the purpose of illustrating various embodiments of the invention.

EXAMPLES

Experimental Procedures

Figure 1:
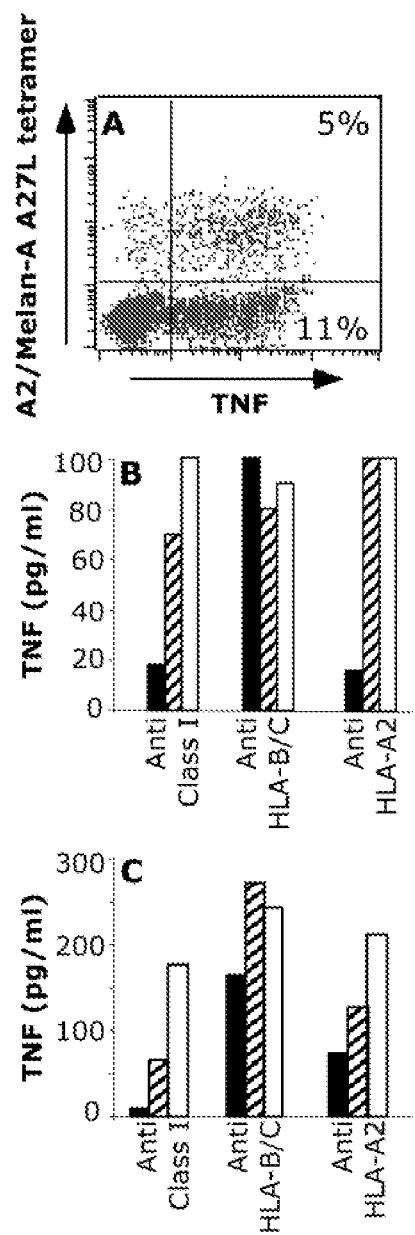
FIG. 1. T cell clone selection and characterization. (A) % of TNF producing T cells and of HLA-A2/Melan-$A_{427L}$ tetramer positive T cells in M170 TIL population in response to the autologous melanoma cell line. $10^5$ TIL and $2.10^5$ melanoma cells were incubated for 5 hours, in the presence of Brefeldin A, stained with HLA-A2/Melan-$A_{427L}$ tetramer, fixed, and stained with anti-TNF antibody in a permeabilization buffer. $10^4$ T cells were then analyzed by flow cytometry. (B and C) TNF secretion by M170.48 T cell clone (B) and M170.51 CTL clone (C) in response to the autologous melanoma cell line. $10^4$ CTL were added to $3.10^4$ M170 melanoma cells, in presence of blocking antibodies directed against class I, A2 and B/C HLA, diluted to 1/50 (black bars), 1/500 (hatched bars) and 1/5000 white bars. CTL clonereactivity was assessed by a TNF release assay.

Material and Methods
Cell Lines and TIL Cultures

T cell populations were expanded from cryopreserved samples of TIL (derived from tumor invaded lymph nodes) infused to melanoma patients included in a phase I/II protocol. This clinical trial aimed at comparing the survival of stage III melanoma patients randomly treated by IL-2 alone or TIL+IL-2, in an adjuvant setting (16). TIL samples were expanded according a procedure previously described (32, 33). TIL containing tumor specific T cells were cloned by limiting dilution (34) and tumor specific T cell clones were amplified as previously described (33). Melanoma cells lines and colorectal carcinoma cell line C4-A were established respectively in the Unit of cellular therapy and in our laboratory. Mouse fibrosarcoma WEHI 164 clone 13 and COS-7 cells were obtained from T. Boon (LICR, Brussels, Belgium). Ovary carcinoma cell lines (OVCAR-3, 0114) and renal carcinoma cell line A498 were gift from C. Saï (INSERM U892, Nantes, France). Colorectal carcinoma cell lines (CaCo-2, Sw480, Sw707, LS174T), renal carcinoma cell line HTC116, breast carcinoma cell line 734-B, were gifts from M. Grégoire (INSERM U601, Nantes, France), S. Chouaib (INSERM U487, Villejuif, France) and D. Jäger (Klinik and Poliklinik für Onkologie, Zürich, Germany). Breast cancer cell line MCF-7 was obtained from the ATCC. Normal melanocytes (98M09 and 01M08), were gifts from M. Regnier (L'Oréal Laboratory, Paris, France). EBV-B cell lines were gifts from H. Vié (INSERM U601, Nantes, France).

Functional Analysis of T Cells

Cytotoxic activity of T cells was measured in a standard 4-h assay against $^{51}$Cr-labeled cells (peptide-loaded T2 cells or tumor cell lines) (23). Measurement of TNF produced by T cells in response to tumor cells or transfected COS-7 cells (19) was performed as previously described, using WEHI 164 clone 13 cells (35). mAb against HLA class I (clone W6.32), HLA-B/C (clone B1.23.2), HLA-A2 (clone BB7.2) added to cultures in some experiments, were produced in our laboratory from hybridomas obtained from the ATCC for W6.32 and BB7.2 antibodies and from F. Lemonier (Pasteur Institute, France) for B1.23.2 antibody. Intracellular staining of cytokines was performed as previously described on stimulated T cells (36). For intracytoplasmic cytokine staining, after a 6 h-stimulation period with melanoma cells at an E:T ration of 1:2, in presence of brefeldin A at 10 µg/mL (Sigma, St Louis Mo., USA), T cells were labeled with an APC-coupled anti-CD8 antibody (BD Biosciences, France), and fixed for 10 min at room temperature in PBS 4% paraformaldehyde (SIGMA). Fixed lymphocytes were stained for cytokine production using anti-TNF-α, anti-IFN-γ, anti-GM-CSF and anti-IL2 specific antibodies (BD Biosciences, France), as previously described. After staining, cells were resuspended in PBS and analyzed on a LSR flow cytometer using Cell Quest software.

cDNA Library and ORFs Constructs

The M134 cDNA library have been inserted in pcDNA3.1 as described previously (20) and recombinant plasmids were electroporated into *Escherichia coli* XL1 (Stratagene). For screening, 800 pools of 100 ampicillin-resistant bacteria were constituted. Plasmid DNA was extracted from each pool with the QIAprep Spin Miniprep kit (QIAGEN). The positive plasmid was sequenced by the DNA Sequencing Facility of the IFR 26 (Nantes, France). The various ORFs from meloe sequence were generated by PCR (see Table I for primers). Oligonucleotides were designed with EcoRI and XhoI adaptators for subcloning in pcDNA3, and with a Kozak sequence (gccaccATG) for upper primer, and a stop codon for lower primer.

Synthetic Peptides

Peptides were purchased from Eurogentec (Angers, France). Purity (>70% or >90% for tetramer production) was controlled by reversed-phase high-performance liquid chromatography. Peptides were lyophilized, dissolved in DMSO at 10 mg/mL and stored at −20° C.

Real-Time PCR

Total RNA was extracted from tumor cell lines, melanocytes and B-EBV cell lines by Trizol reagent (Invitrogen, Cergy Pontoise, France). RNA from healthy tissues were purchased from Clontech (France). Quality of RNA samples was controlled using an Agilent bioanalyzer and all the samples exhibited a RIN>7. Retrotranscription was performed using 1 μg of total RNA, random hexamers and SuperScript II reverse transcriptase (Invitrogen). Relative quantification of meloe, RPLPO and β2-microglobulin expression was carried out using Brilliant SYBR Green QPCR in the Mx4000 (Stratagene Europe, Amsterdam, The Netherlands). 10 ng of cDNA from samples were added to SYBR green master mix (Stratagene for Mx4000) with forward and reverse primers (Table I) at 200 nM in a final volume of 25 μL. Thermal cycling was one step at 95° C. for 10 min, followed by 40 cycles at 95° C. for 30 s, 63° C. for 1 min and 72° C. for 1 min. The efficiency of PCR reaction was determined with series of 10-fold diluted cDNA from M170, performed in parallel to plot the standard curves for meloe, RPLPO and β2-microglobulin. Duplicate dilution series were included as standards in each run. Average threshold cycle (CT) values from duplicate PCR reactions were normalized to average CT values for two housekeeping genes (β2-microglobulin and RPLPO) from the same cDNA preparations. The relative expression ratio of a target gene was calculated based on the PCR efficiency (E) and the CT deviation between a given cell line (x) and a reference cell line (calibrator), expressed in comparison with the mean of the housekeeping genes (37).

$$\text{Ratio} = (E\text{target})^{\Delta CT_{target}(calibrator-x)} / \text{mean}((E\text{house-keeping})^{\Delta CT_{housekeeping}(calibrator-x)})$$

Tetramer and Vβ Labeling

HLA-A*0201/MELOE-1 and HLA-A*0201/Melan-A α3-mutated monomers were generated by the recombinant protein facility (INSERM U892, Nantes, France), as previously described (38). TIL populations and M170.48 T cell clone were coincubated for 1 h at 4° C. in the dark with MELOE-1 tetramer (10 μg/mL) and CD8 mAb (5.1 μg/mL) and $10^4$ events were analyzed on a FACSCalibur. A panel of 25 anti-Vβ mAbs (Vβ1, −2, −3, −4, −5.1, −5.2, −5.3, −6, −7, −7.2, −8, −9, −11, −12, −13.1, −13.2, −13.6, −14, −16, −17, −18, −20, −21.3, −22 and −23) was used to analyse the diversity of sorted TIL populations (Immunotech Beckman-Coulter, Marseille, France).

Immunomagnetic Cell Sorting and Expansion of T Cell Sorted Populations

HLA-A*0201/MELOE-1 monomers (20 μg/mL) were incubated for 1 h at room temperature with $6.7.10^6$ streptavidin-coated beads (Dynabeads M-280 streptavidin, DYNAL, Compiegne, France) and washed in PBS-0.1% BSA. $5.10^6$ TIL were rotated for 4 hours at 4° C. with monomer-coated beads (23, 38). After ten washes, bead coated cells were expanded using a polyclonal T cell stimulation protocol (33). Frequency and Status of MELOE-$1_{36-44}$ Specific T Cells in HLA-A*0201 Healthy Donor and Melanoma Patient PBMC.

$10^8$ PBMC were collected from HLA-A2 healthy donors (EFS, Nantes, France) or from HLA-A2 melanoma patients (gift from D. Schadendorf, University of Essen, Germany and B. Dreno, Nantes hospital, France). Labeling with PE-conjugated tetramers and sorting were performed according to a method recently described (42). PE-conjugated MELOE-1 tetramer was added at a concentration of 50 μg/mL, and the cells were incubated at 4° C. for 1 hr, followed by two washes in 15 ml of ice-cold buffer (PBS+0.1% BSA). The tetramer-stained cells were then resuspended in a volume of 0.9 mL of buffer, mixed with 0.1 mL of anti-PE antibody conjugated magnetic microbeads (Miltenyi Biotech, France) and incubated at 4° C. for 30 min, followed by two washes with 10 mL of sorter buffer. The cells were then resuspended in 3 mL of buffer and passed over a magnetized LS column (Miltenyi Biotech, France). The column was washed with 3 mL of buffer three times and then removed from the magnetic field. The bound cells were eluted by pushing 5 ml of sorter buffer through the column with a plunger. The resulting enriched fractions were resuspended in 0.5 mL of sorter buffer, and a small volume was removed for cell counting while the rest of the sample was stained with a cocktail of fluorochrome-labeled antibodies specific for CD14, CD16, CD19, CD8, CD45RA, CD27, CD28, CD62-L and CD127 (BD Biosciences, France). The entire stained sample was then collected on an Facs Canto (BD Immunocytometry Systems) and analyzed with FlowJow software. The percentage of tetramer-positive cells among CD8$^-$ lymphocytes was estimated from the number of tetramer-positive cells in the enriched fraction and from the fraction of CD8+ cells in total PBMC.

Functional Analysis of T Cells

The relative avidity of MELOE-$1_{26-44}$ specific T cell clones and their anti-tumor reactivity was measured respectively in a standard 4-h assay against $^{51}$Cr-labeled peptide-loaded T2 cells and towards HLA-A2 melanoma cell lines. Briefly, target cells (peptide pulsed-T2 or melanoma cells) were incubated with 100 μCi Na$_2$$^{51}$CrO$_4$ (Oris Industrie, Gif-sur-Yvette, France) at 37° C. for 1 h. For peptide recognition assays, T2 cells were preincubated with a range of MELOE-$1_{26-44}$ peptide concentrations for 1 h at 37° C. After the 4 h-co-culture, 25 μL of supernatant were mixed with 100 μL of scintillation cocktail (Optiphase Supermix, Wallak, UK) for measurement of radioactive content. EC50 were compared using statistical analysis done with InStat 2.01. Data were analyzed using Kruskal-Wallis comparison test, followed by Dunn'post test. P<0.05 was considered significant.

Results

T Cell Clone Selection and Characterization.

M170 TIL population contained 16% of melanoma-reactive lymphocytes, among them 5% were specific of Melan-A/A2 epitope and 11% were of unknown specificity (FIG. 1A). This TIL population was then tested for recognition of a large panel of known antigens transfected into COS cells, with the class I HLA molecules of M170 patient (19), and no response aside from Melan-A/A2 response could be detected (data not shown), suggesting that this population contained lymphocytes specific for new tumor antigen(s). In order to characterize them, we derived tumor reactive CD8$^+$ T cell clones by limiting dilution. Eight of these CTL clones showed reactivity patterns consistent with recognition of (a) new antigen(s) and two of them, hereafter referred to as M170.48 and M170.51, were further characterized in order to determine the HLA context restricting its recognition. As illustrated by FIGS. 1B and 1C, the recognition of the autologous melanoma cell line by these two CTL clones occurs in the HLA-A2 context. In order to establish the distribution of the target antigen, we tested T cell clone reactivity towards various HLA-A2 tumor cell lines including melanomas, ovarian carcinomas, lung carcinomas, breast carcinomas, renal carcinomas and colon carcinomas, using a TNF release assay. As shown in FIGS. 2a and 2B, these T cell clones recognized all the HLA-A2 melanoma cell lines tested but none of the other HLA-A2 tumor cell types. In addition, these two T cell clones cell clone weakly recognized HLA-A2 melanocytes (FIG. 2C). However, this reactivity was much lower than that usually seen with Melan-A/A2 specific T cell clones (data not shown).

Identification of the cDNA Coding for the Antigen.

Figure 3:
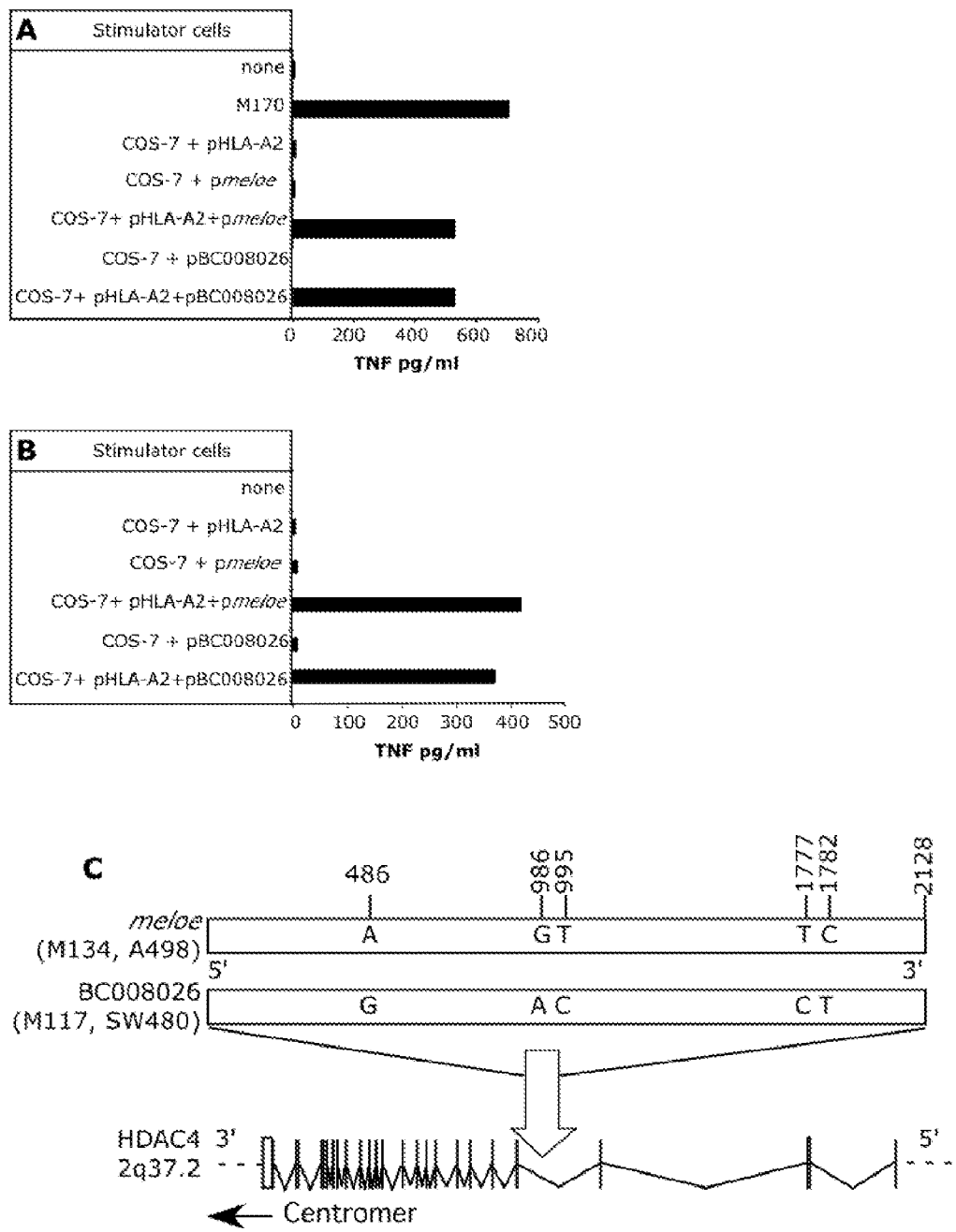
FIG. 3. Characterization of the cDNA coding for the recognized antigen. (A and B) M170.48 (A) and M170.51 (B) TNF responses to COS-7 cells (E/T ratio 1/3) transfected with indicated plasmids. T cell clones were added 2 days after the transfection and the CTL clone reactivity was assessed by a TNF release assay. (C) Comparison of the nucleotide sequences of meloe and BC008026 cDNAs and localization of this sequence on the HDAC4 gene. Indicated nucleotides correspond to SNPs between the meloe sequence isolated from M134 and A498 tumor cell lines and the meloe sequence isolated from M117 and SW480 cell lines, and the BC008026 cDNA sequence.

We screened a cDNA library derived from the M134 melanoma cell line (20) in COS-7 cells cotransfected with pHLA-A*0201 to characterize the Ag recognized by M170.48 and M170.51 T cell clones. Among 800 pools of 100 pcDNA tested, the same plasmid pool proved positive for the two CTL clones, and the individual plasmid, coding for the antigen recognized by M170.48 (FIG. 3A) and M170.51 (FIG. 3B) was recovered from it after a cloning step. This insert, namely meloe, spanning 2128 bp, was sequenced and was found to contain a poly(A) tail and to be similar to the clone BC008026 isolated by the NIH MGC consortium (21). After expression vector cloning, cotransfection of BC008026 cDNA with HLA A*0201 into COS-7 also induced the recognition by M170.48 and M170.51 T cell clone (FIGS. 3A and 3B), although these two sequences differed by four SNPs (FIG. 3C). In order to control the impact of these SNPs on the recognition of the two T cell clones, we sequenced the cDNA isolated from recognized (M134, M117) and non recognized cell lines (A498, SW480), and showed that this polymorphism did not affect tumor cell line recognition. The meloe sequence analysis showed a perfect colinearity with the genomic DNA, obtained by comparison with the sequence of the human genome released by Celera (22), which indicated absence of splicing. Finally, this sequence was found to be located in the third intron of the HDAC-4 gene (Gene ID #9759), on chromosome 2, in anti-sense orientation compared to the sequence of the HDAC-4 gene.

Identification of the Peptides Recognized by M170.48 and M170.51 T Cell Clones.

Figure 4:
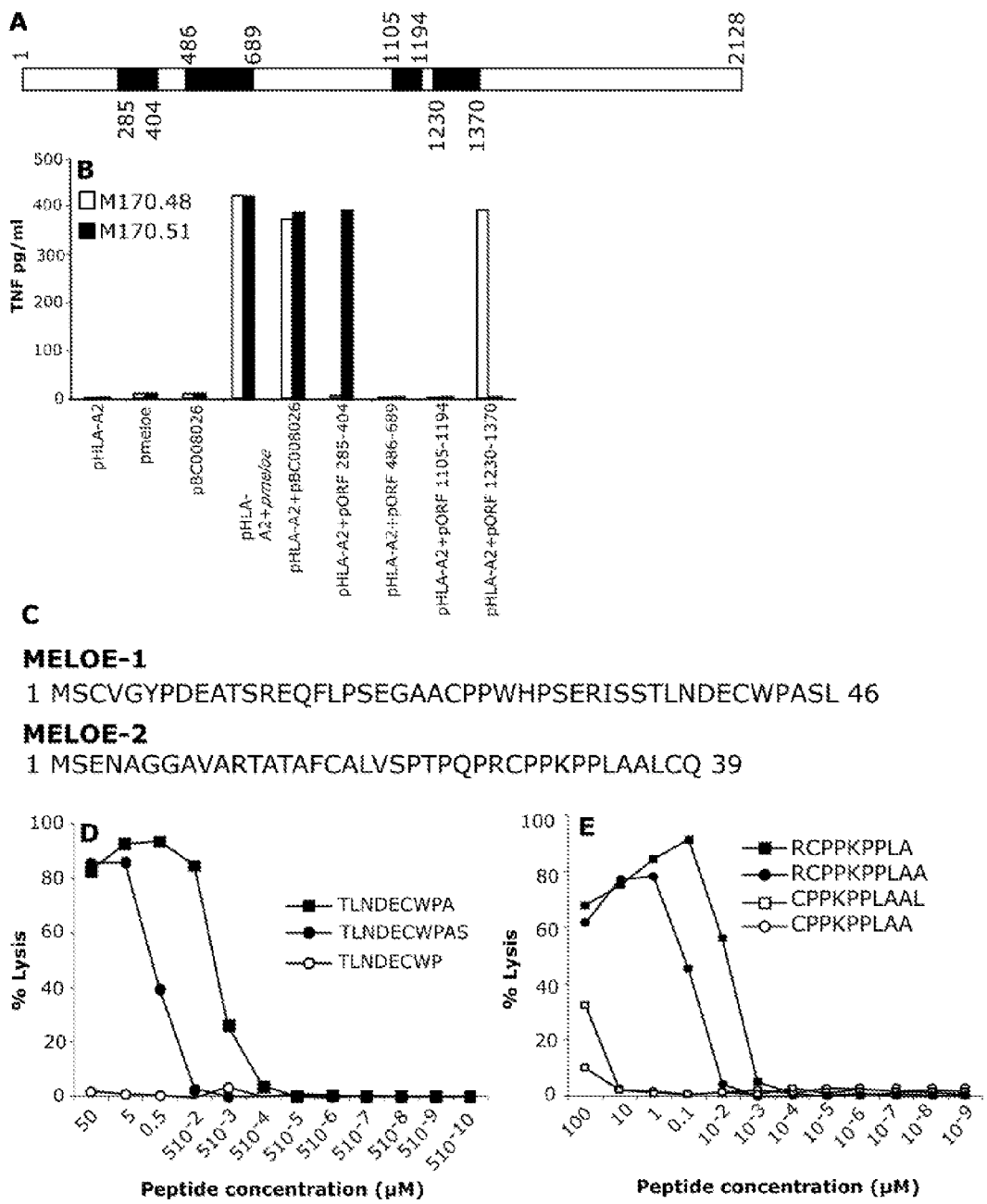
FIG. 4. Characterization of meloe derived peptides recognized by M170.48 and M170.51 T cell clones. (A) Structure of meloe cDNA. Black boxes correspond to ORFs tested for recognition by the CTL clone. (B) M170.48 and M170.51 TNF responses to COS-7 cells (E/T ratio 1/3) transfected with indicated plasmids. T cell clone was added 2 days after the transfection and the CTL clone reactivity was assessed by a TNF release assay. (C) Amino acid sequences of the ORF 1230-1370 and the ORF 285-404 of meloe isolated from M134 cDNA library. (D and E) Cytotoxicity of M170.48 CTL clone (D) and M170.51 CTL clone(E) against peptide-pulsed T2 cells. Target cells were chromium labeled for 60 min and incubated for 30 min with a range of the indicated peptides. T cell clones were added at an E/T ratio of 10/1 and chromium release was then measured after a 4 h incubation period.

The meloe cDNA does not contain a long ORF, but multiple short ORFs (FIG. 4A). The putative ORF described by the NIH MGC consortium was located between 486 and 689 bp (21). We tested this ORF and three additional ORFs (black boxes in FIG. 4A), for recognition by M170.48 and M170.51, after transfection into COS-7 cells, with the HLA-A*0201 cDNA (FIG. 4B). The ORFs tested were chosen on the basis of preliminary results obtained on PCR fragments of meloe (data not shown).

The ORF 1230-1370 bp encodes the protein bearing the peptide recognized by the specific M170.48 T cell clone, and the ORF 285-404 bp encodes the protein bearing the peptide recognized by the specific M170.51 T cell clone (FIG. 4C). These ORFs respectively encode a 46 and a 39 amino-acids protein. We tested the recognition of various peptides derived from these two sequences able to bind to the HLA A*0201, with a high stability as predicted by BIMAS analysis (http://www-bimas.cit.nih.gov).

Two nonapeptides, were tested for their recognition by M170.48 T cell clone, after loading on T2 cells. Only the sequence 36-44 <<TLNDECWPA>> was recognized (FIG. 4D and data not shown). We then tested the recognition of two additional peptides derived from this nonapeptide. We observed that addition of the serine at the C-terminus (position 45) dramatically decreased the response of our CTL clone (black circles on FIG. 3D) and that deletion of the alanin at the C-terminal end (position 44) abrogated the CTL clone response (open circles on FIG. 4D). In conclusion, the optimal peptide recognized by M170.48 CTL clone appeared to be the nonapeptide 36-44 (TLNDECWPA), with a half maximal lysis of $10^{-8}$M (black squares on FIG. 4D).

Several nonapeptides were tested for their recognition by M170.51 T cell clone, after loading on T2 cells. Only the sequence 27-35 <<RCPPKPPLA>> was recognized (FIG. 4E and data not shown). We then tested the recognition of additional peptides derived from this nonapeptide. We observed that addition of the alanin at the C-terminus (position 36) dramatically decreased the response of our CTL clone (black circles on FIG. 4E) and that deletion of the arginin at the N-terminal end (position 27) abrogated the CTL clone response (open circles on FIG. 4D), even when the leucin was added at the C-terminal end (open squares on FIG. 4D). In conclusion, the optimal peptide recognized by M170.51 CTL clone appeared to be the nonapeptide 27-35 (CPPKPPLA), with a half maximal lysis of $5.10^{-8}$M (black squares on FIG. 4D).

Meloe is Overexpressed in Melanomas

Figure 5:
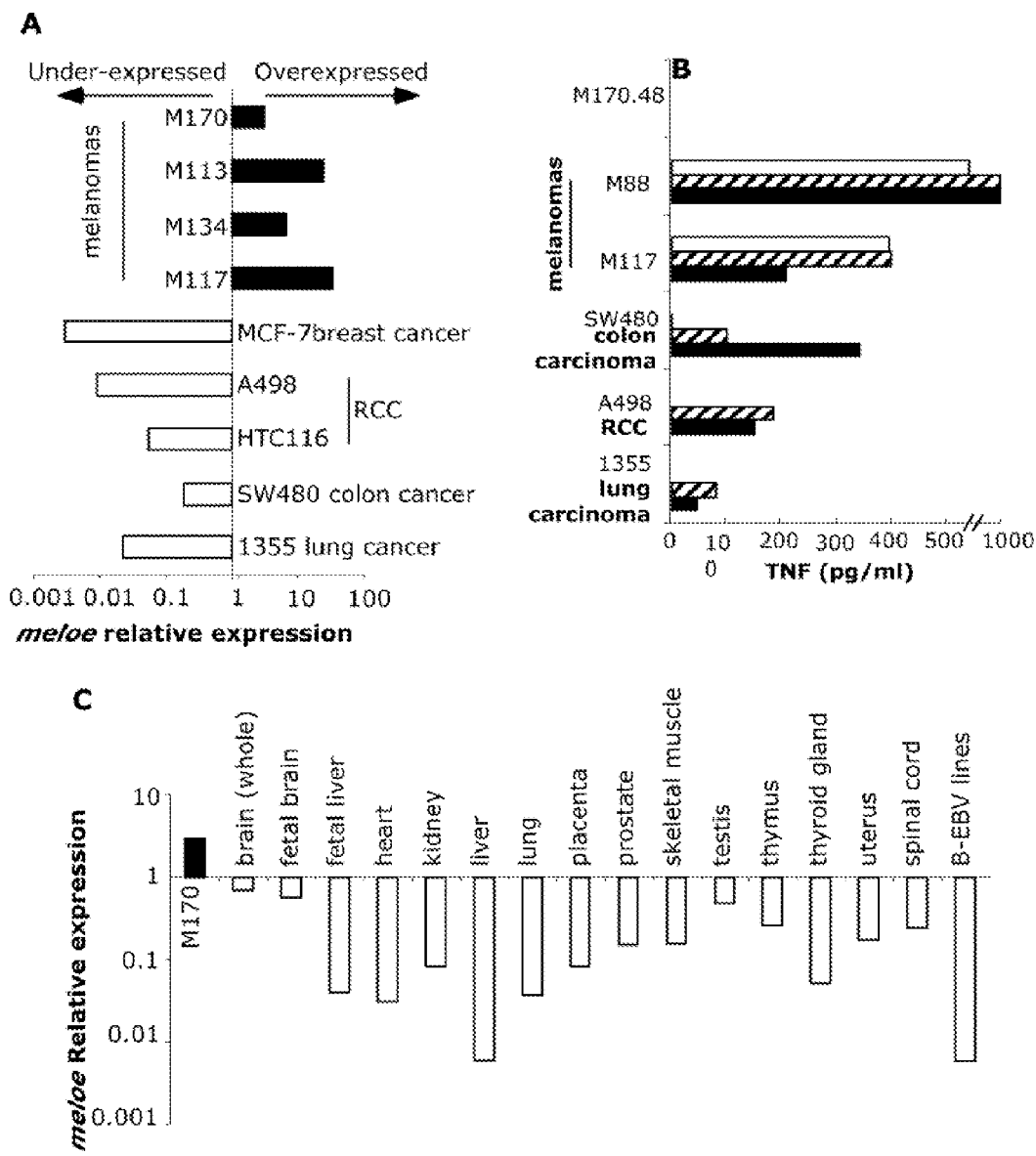
FIG. 5. Preferential expression of meloe cDNA in melanoma cell lines measured by qPCR, and impact of meloe expression on specific CTL clone activation. (A) Four melanoma, one breast cancer, two renal carcinoma and one lung cancer cell lines were tested by qPCR for the expression of meloe. RPLPO and β2 microglobulin gene expression were used as internal controls. The relative expression of meloe was calculated after normalization on the efficiency of PCR reaction and the mean expression of these two house-keeping genes, reported to its normalized expression in melanocytes. (B) TNF secretion by the M170.48-CTL clone in response to HLA-A2 tumor cell lines non transfected (white bars), or transfected with meloe (hatched bars) or meloe-1 (black bars) expression plasmids. Tumor cells were transiently transfected with 100 ng of each plasmid, with a lipofectamine reagent kit. $10^4$ CTLs were added to $3.10^4$ target cells, and the CTL clone reactivity was assessed by a TNF release assay. (C) meloe relative expression measured by qPCR in 16 human healthy tissues.

In order to explain the absence of recognition of tumor cell lines other than melanomas, we compared the transcription level of meloe cDNA by qPCR in a panel of HLA-A2 tumor cell lines and melanocytes. The mean level of meloe expression in two HLA-A2 melanocytes was used as a reference to establish its relative expression in other cell lines. This analysis showed that meloe expression in melanomas was higher than in melanocytes, with values ranging from 3 to 34 fold higher, whereas this expression was significantly lower in other tumor cell lines, with values ranging from 5 to 338 fold lower (FIG. 5A). These results show that this antigen is overexpressed in melanomas and thus proteins encoded by the ORF 1230-1370 and 285-404 were respectively called "MELOE-1" for "melanoma-overexpressed antigen-1" and MELOE-2 for "melanoma-overexpressed antigen-2". Furthermore, transfection of meloe or meloe-1 cDNA in HLA-A2 non recognized tumor cell lines induced their recognition by M170.48 T cell clone (FIG. 5B), showing that the absence of recognition of these tumor cell lines was due to the underexpression of meloe cDNA. Finally, in order to address the question of the expression of this antigen in healthy tissues, we performed qPCR on a panel of 16 tissues. It appears that the expression of meloe in healthy tissues was always lower than in melanocytes. The highest meloe expression was found in whole and fetal brain but remained respectively 1.5 and 1.8 fold below its expression in melanocytes (FIG. 4C). Overall, these results suggest that this antigen could be safely targeted in immunotherapy protocols in melanoma, provided that its immunogenicity could be documented.

Figure 6:
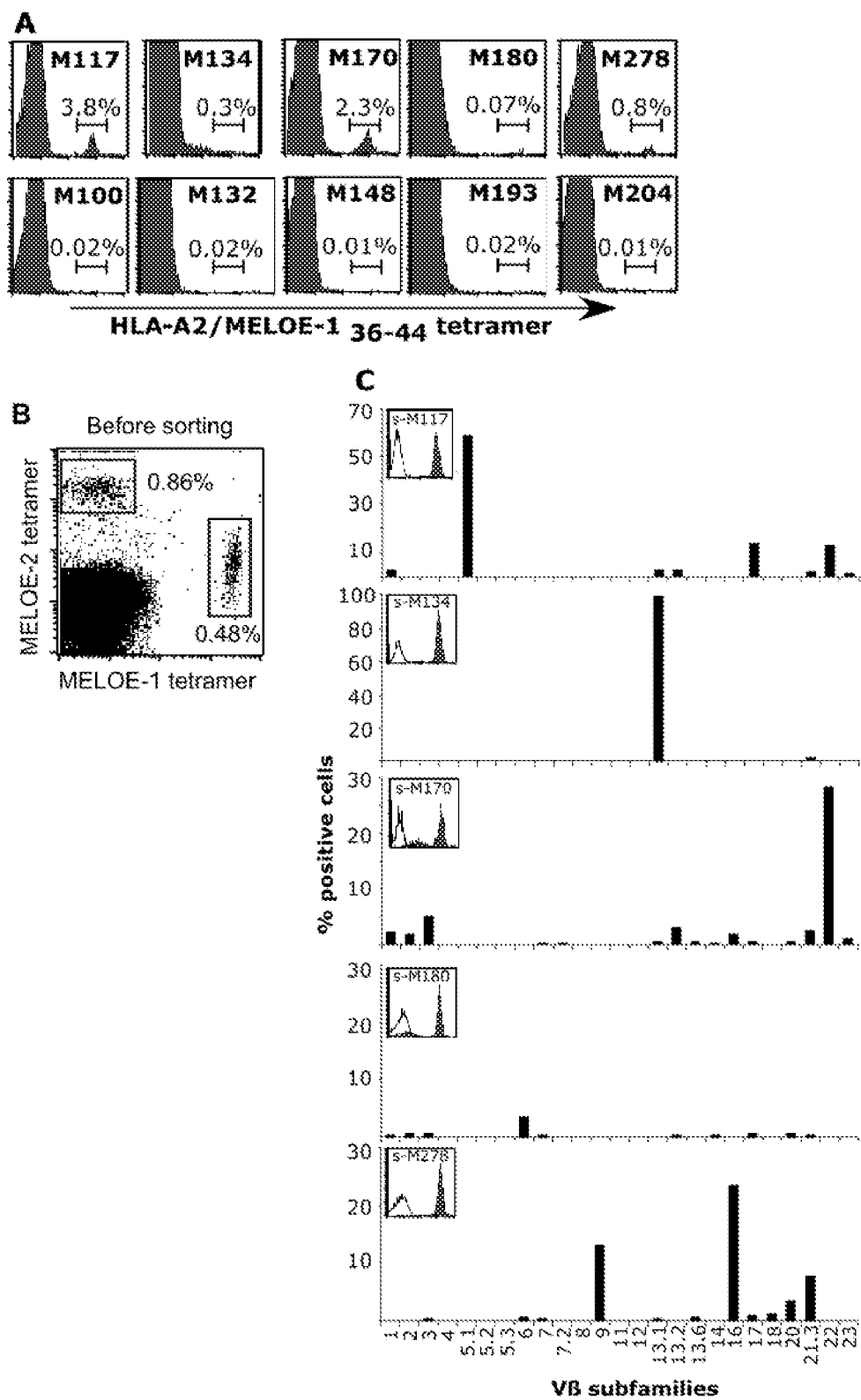
FIG. 6. Detection of MELOE-1/A2 and MELOE-2 specific CTLs in TIL infused to relapse-free melanoma patients and analysis of the repertoire diversity of MELOE-1 specific TIL. (A) HLA-A2 TIL populations labeled with the A2/MELOE-$1_{36-44}$ tetramer. Upper panel: TIL infused to relapse-free patients and lower panel: TIL infused to patients who relapsed. TIL were coincubated with MELOE-1 tetramer and anti-CD8 mAb. Values indicate the % of tetramer positive cells among $CD8^-$ TIL. (B) Labeling of A2/MELOE-$2_{27-35}$ specific T cells in M278 TIL population. TIL were co-labeled with CD8 antibody, A2/MELOE-$1_{36-44}$ and A2/MELOE-$2_{27-35}$ tetramers. Values indicate the fraction of positive T cells among CD8 positive TIL. (C) Repertoire diversity of multimer-sorted populations was evaluated by labeling with 25 anti-Vβ mAbs. Inserts illustrate the purity of each sorted TIL population, assessed by MELOE-1 specific tetramer labeling.

Presence of MELOE-1 Specific Lymphocytes in TIL Populations Infused to Relapse-free Patients In order to address the question of the immunogenicity of this new epitope, we used a specific HLA-A2/peptide tetramer to look for the presence of specific lymphocytes among 30 HLA-A2 TIL populations derived from melanoma invaded lymph nodes. All those TIL populations had been infused to melanoma patients in an adjuvant setting, between 1998 and 2002. Following this treatment, 21 of these patients relapsed and 9 remained relapse-free. Using a specific HLA/peptide tetramer, we detected the presence of MELOE-1/A2 specific T cells in 5/9 TIL populations that had been infused to relapse-free patients, with frequencies ranging from 0.07% to 3.8% among CD8+ TIL (FIG. 6A, upper panel). In contrast, we did not observe the presence of such T cells among the TIL infused to the 21 HLA-A2 patients who relapsed. An example of 5 out of these 21 negative TIL populations is shown on FIG. 6A, lower panel. These results document the existence of a correlation between the presence of MELOE-1 specific lymphocytes among infused TIL and relapse prevention (p<0.001), and thus suggest the potential immunogenicity of this new HLA-A2 melanoma epitope. We also detected MELOE-2 specific T cells in M278 TIL population, which also contains MELOE-1 specific lymphocytes (FIG. 6B).

Figure 7:
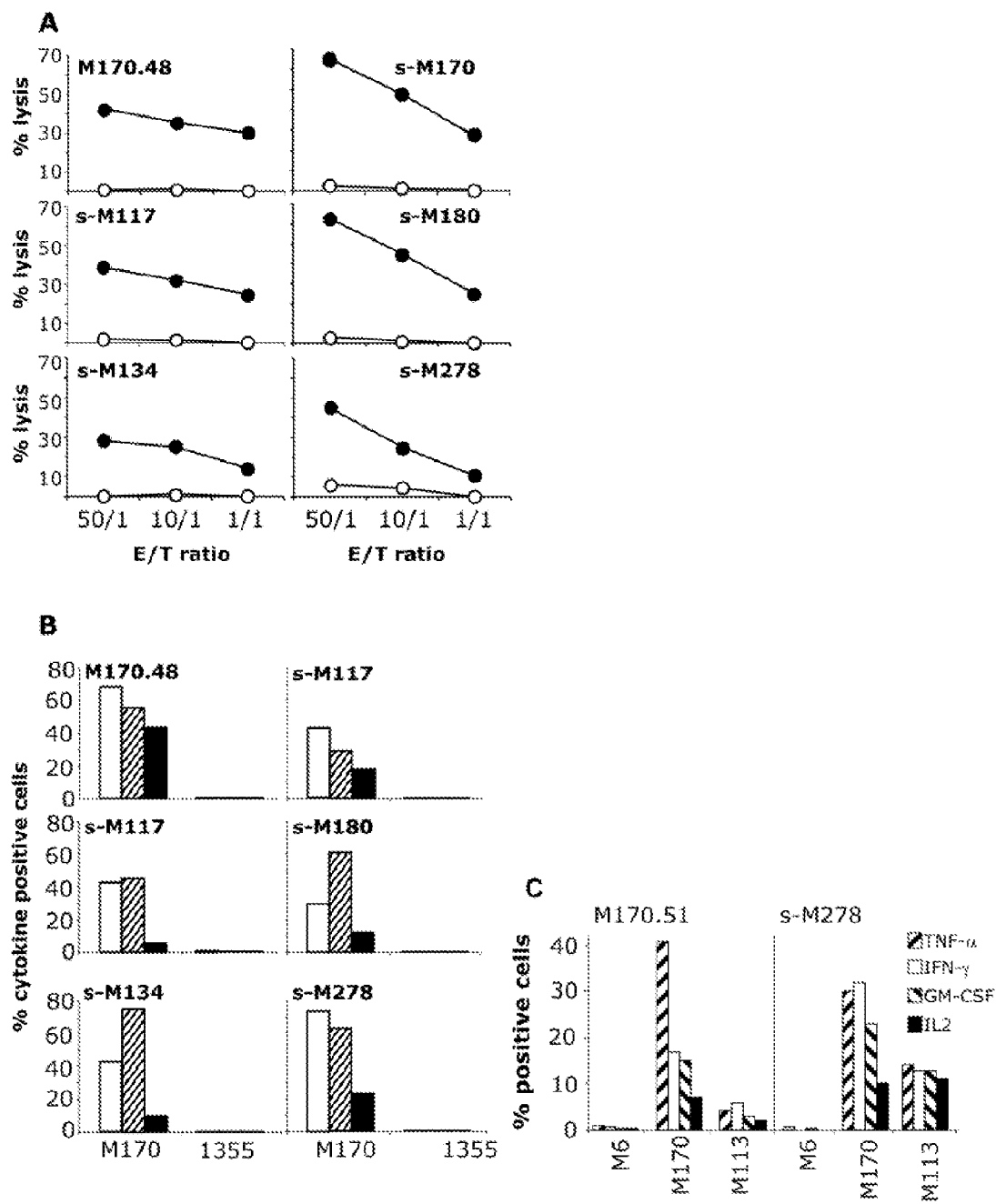
FIG. 7. Reactivity of MELOE-1/A2 and MELOE-2 specific TIL against HLA-A2 tumor cell lines (A) Lysis of M170 melanoma cell line (black symbols) and of 1355 lung carcinoma cell line (open symbols) by M170.48 CTL clone and MELOE-1 specific TIL populations. $^{51}$Cr-labeled tumor cells were co-cultured with T cells at various E/T ratios. Chromium release in the supernatants was measured after a 4 h incubation period. (B) Cytokine production by M170.48 CTL clone and MELOE-1 specific TIL populations in response to M170 melanoma cells. Effector and target cells were incubated at a 1/2 ratio in the presence of Brefeldin A, stained with anti-TNF antibody (white bars), anti-IFN-γ antibody (hatched bars) or anti-IL2 antibody (black bars), and $10^4$ T cells were analyzed by flow cytometry. (C) Production of TNF-α, IFN-γ, GM-CSF and IL-2 by the MELOE-2 specific T cell clone (M170.51) and the MELOE-2 sorted specific population (s-M278), in response to two HLA-A2 positive melanoma cell lines and a HLA-A2 negative melanoma cell line.

Finally, in order to address the question of the diversity and tumor reactivity of the MELOE-1/A2 specific repertoire, specific lymphocytes were sorted by monomer-based immunomagnetic sorting (23), from the 5 positive TIL populations. Inserts on FIG. 6B illustrate the purity of sorted TIL, assessed by specific tetramer labeling. We also attempted to sort 5 negative TIL populations with monomer-coated beads, but no MELOE-1 specific cells were obtained (data not shown). This last result formally documented the absence of such cells in those populations, or at least showed that the frequencies of MELOE-1 specific T cells were too low to allow their purification by multimer sorting. The diversity of TCR Vβ usage of sorted populations was assessed with a panel of 25 anti-Vβ antibodies representing the most frequently expressed Vβ chains within a normal repertoire. In M117, M170 and M278 sorted populations, 8 or 6 different Vβ chains were significantly expressed (above 1%) by MELOE-1/A2 specific TIL, indicating the presence of a rather polyclonal specific TCR repertoire (FIG. 6C). TCR diversity of M134 sorted TIL was much lower, with a strong dominance of lymphocytes expressing the Vβ13.1 chain (FIG. 6C). This may be related to the low fraction of MELOE-1 specific T cells present in this population before sorting (0.3% of CD8+ TIL, FIG. 6A), probably poorly diverse. Finally, we could not determine the dominant Vβ chain expressed by TIL sorted from M180, with our panel of antibodies. Therefore, no dominant Vβ usage could be observed within these three sorted TIL populations. Finally, in order to support the potential role of MELOE-1/A2 specific TIL transfer in relapse prevention, we studied the reactivity of sorted TIL populations on HLA-A*0201 melanoma cell lines that spontaneously express the MELOE-1 antigen. All sorted T cell lines were lytic against melanoma cell lines (FIG. 7A and data not shown) and produced IFN-γ and TNF upon stimulation by these cells, with levels similar to M170.48 CTL clone, and to a lower extent IL-2 (FIG. 7B and data not shown). MELOE-2 specific lymmphocytes sorted from M278 TIL population were also reactive against HLA-A2 melanoma cell lines, as illustrated by cytokine production in response to a stimulation with M170 HLA-A2 melanoma line (FIG. 7C).

Frequency and Status of MELOE-$1_{36-44}$ Specific T Cells in HLA-A2 Healthy Donors and Melanoma Patients PBMC and TIL.

Figure 8:
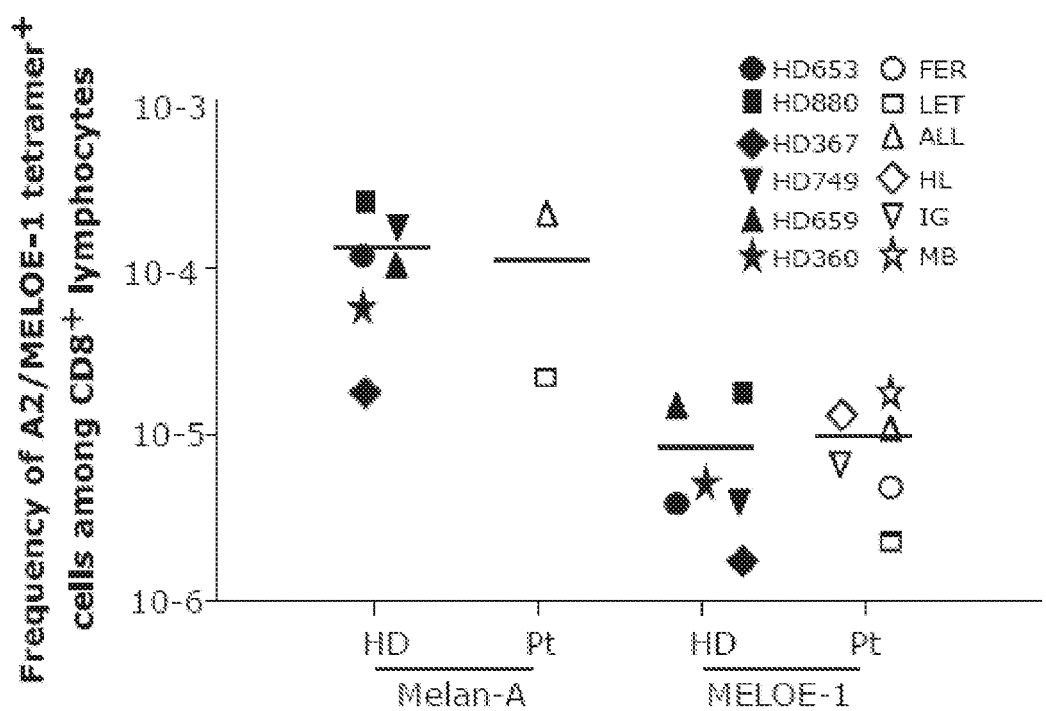
FIG. 8. Frequencies of MELOE-1$_{36-44}$ and Melan-A$_{A27L}$ specific T cells among PBMC from HLA-A2 healthy donors and melanoma patients. About $10^8$ PBMC were sorted with PE-conjugated tetramers according a method recently described (42). The entire stained sample was then collected on an Facs Canto (BD Immunocytometry Systems) and analyzed with FlowJow software. The percentage of tetramer-positive cells among CD8$^+$ lymphocytes was estimated from the number of tetramer-positive cells in the enriched fraction and from the fraction of CD8$^+$ cells in total PBMC. On healthy donors, the frequencies of Melan-A$_{A27L}$/A2 specific lymphocytes were also estimated, as an internal control of the sorting method.

$10^8$ PBMC were sorted by tetramer labeling according the method described by Moon et al. (20). Sorted cells were immediately analyzed by multicolor staining The frequency of MELOE-1 specific T cells among CD8+ lymphocytes was deduced from the total number of CD8/tetramer positive sorted cells and the total number of CD8 lymphocytes among PBMC before sorting. As a control, we performed the same analysis on Melan-A specific CD8 T cells. The number of tetramer positive cells recovered after the sorting step ranged between 50 and 400 for MELOE-1 specific cells and between 400 and 4000 for Melan-A specific cells. Concerning healthy donors, the frequency of MELOE-$1_{26-44}$ specific T cells among CD8+ cells ranged from $1.8 \cdot 10^{-6}$ to $1.8 \cdot 10^{-5}$, whereas that of Melan-$A_{A27L}$ specific T cells ranged from $1.8 \cdot 10^{-5}$ to $2.5 \cdot 10^{-4}$ (FIG. 8, black symbols). The frequencies observed in melanoma patients were rather similar, ranging from $2.2 \cdot 10^{-6}$ to $1.7 \cdot 10^{-5}$ for MELOE-1 specific T cells and from $2.2 \cdot 10^{-5}$ to $2 \cdot 10^{-4}$ for Melan-A specific lymphocytes (FIG. 8, open symbols). CD8/MELOE-1 specific T cells were then phenotyped for CD45RA, CD62L, CD28 and CD27 by mutiparametric flow cytometry (43, 44).

Figure 9:
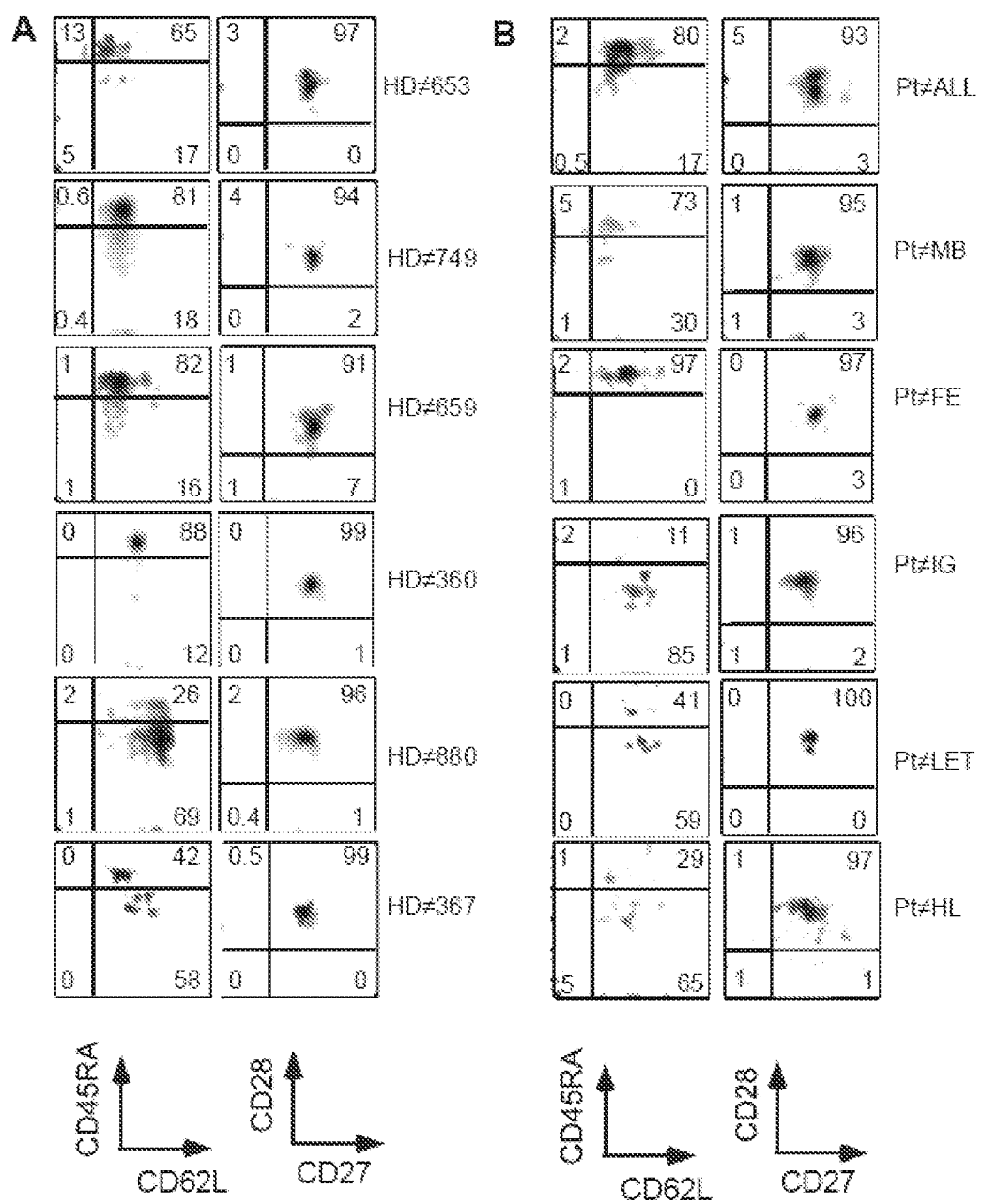
FIG. 9. Phenotypic analysis of ex-vivo circulating A2/MELOE-1 specific T cells in healthy donors and melanoma patients. After sorting with PE-conjugated tetramers, the lymphocyte preparations were stained with a cocktail of Pacific blue-conjugated exclusion markers (CD14, CD16, CD19), CD8$^{AmCy}$, CD45RA$^{PE-Cy7}$, CD27$^{APC-H7}$, CD28$^{PerCP-Cy5.5}$, and CD62-L$^{FITC}$, and immediately analyzed by flow cytometry. (A and B) Pattern of expression of CD45RA/CD62L (left) or CD28/CD27 (right) gated on CD8/MELOE-1 double positive T cells, from healthy donors (A) and melanoma patients (B). Numbers indicate the fraction of healthy donors or melanoma patients with the corresponding phenotype.

Circulating A2/MELOE-1 CD8+ T cells detected in 4/6 healthy donors presented a predominant naive phenotype (CD45RA$^{hi}$/CD28$^-$/CD27$^+$/CD62L$^+$), (FIG. 9A), while in 2/6 donors, tetramer+ cells displayed high proportions (69 and 58%) of memory T cells (CD45RA$^{low}$/CD28$^+$/CD27$^+$/CD62L$^+$) (FIG. 9A). Concerning melanoma patients, we also observed these two different phenotypes. Indeed, MELOE-1 specific T cells from 3/6 patients mainly displayed a naive phenotype (FIG. 9B). In contrast, in the remaining 3 patients, 59 to 85% of A2/MELOE-1 specific cells displayed a memory phenotype.

Relative Avidity and Tumor Reactivity of MELOE-1 Specific T Cell Clones

Figure 10:
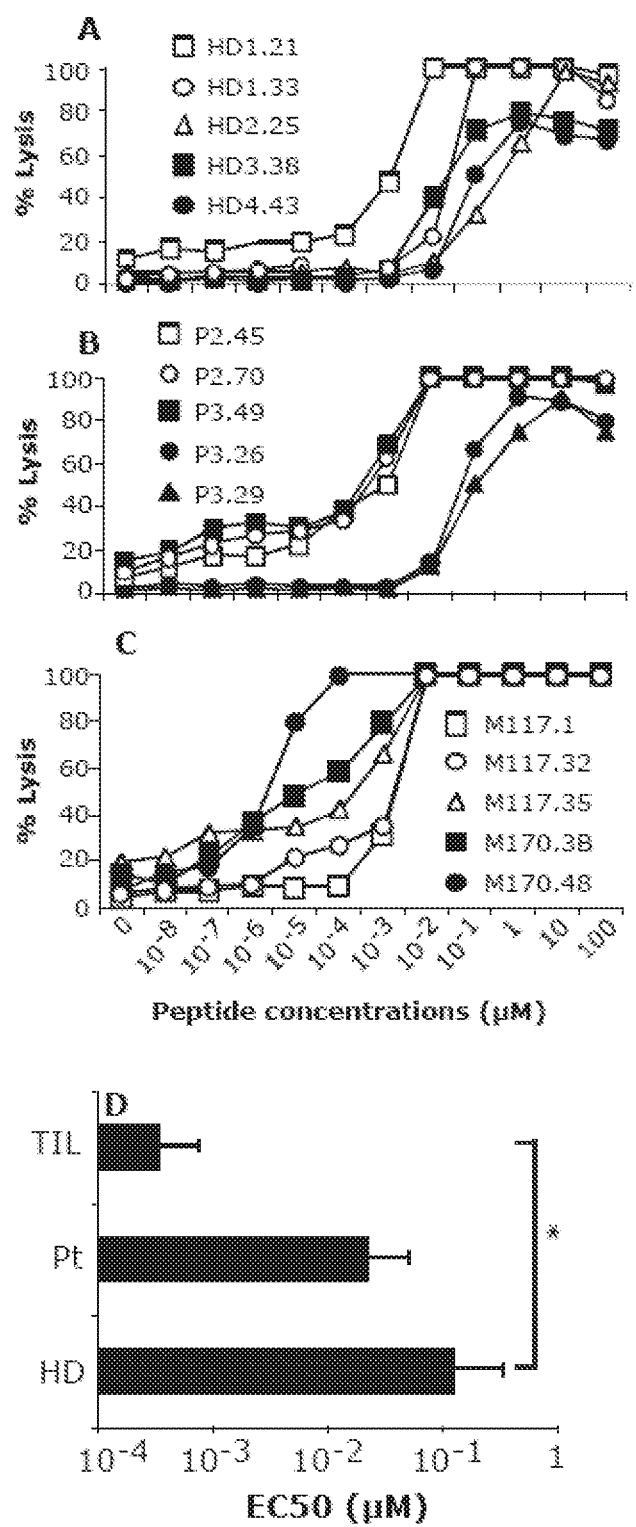
FIG. 10. Cytotoxicity of MELOE-1 specific CTL clones against peptide-pulsed T2 cells. Target cells were chromium labeled for 60 min and incubated for 30 min with a range of the MELOE-1$_{36-44}$ peptide. T cell clones derived from healthy donors (A), melanoma patients PBMC (B) and TIL (C) were added at an E/T ratio of 10/1 and chromium release was then measured after a 4 h incubation period. (D) Mean EC50 of the MELOE-1 specific T cell clones in response to the MELOE-1$_{36-44}$ peptide, according to their origin. EC50 were compared using statistical analysis done with InStat 2.01. Data were analyzed using Kruskal-Wallis comparison test. *p=0.019, considered significant.

15/18 clonotypes could be further amplified to analyse their avidity for T2 cells loaded with the MELOE-1 specific peptide. As shown on FIG. 4A, the EC50 of the clonotypes derived from healthy donors ranged from 0.5 to $10^{-3}$ μM of MELOE-$1_{36-44}$ peptide (FIG. 10A). The avidity of MELOE-1 specific clonotypes derived from patient PBMC or TIL was less scattered, with EC50 ranging respectively from $5.10^{-2}$ to $4.10^{-4}$ μM and from $8.10^{-4}$ to $8.10^{-7}$ μM (FIGS. 10B and C). Overall, MELOE-1 specific clonotypes derived from melanoma patients appear to have a better avidity towards MELOE-$1_{36-44}$ peptide, than specific clonotypes derived from healthy donors (FIG. 10D), although all express the Vα12.1 chain. This difference was significant (p=0.019) between T cell clones derived from healthy donor PBMC and those derived from melanoma TIL.

Figure 11:
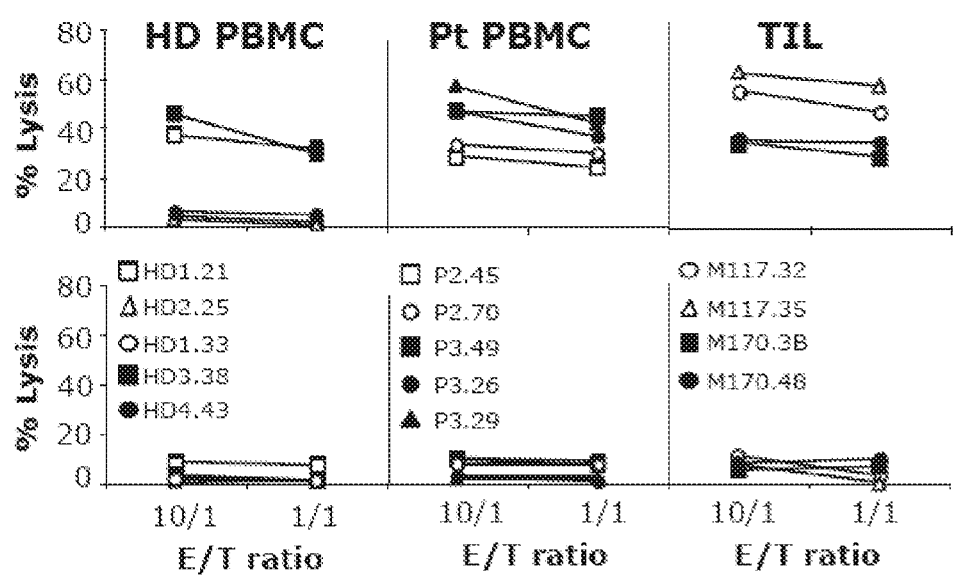
FIG. 11. Lysis of M170 (HLA-A2 positive, upper panel) and M6 (HLA-A2 negative, lower panel) melanoma cell lines by MELOE-1 specific T cell clones derived from healthy donors, melanoma patients PBMC and TIL. $^{51}$Cr-labeled tumor cells were co-cultured with T cells at 10/1 and 1/1 E/T ratios. Chromium release in the supernatants was measured after a 4 h incubation period.

Tumor reactivity of the different clonotypes was then tested on HLA-A2 melanoma cell lines. FIG. 11 illustrates the results obtained on a HLA-A2 positive melanoma cell line (M170: upper panel) and a HLA-A2 negative melanoma cell line (M6: lower panel). M171.1 clonotype could not be tested for tumor reactivity because it failed to be further expanded. All the clonotypes derived from patients (PBMC and TIL) were cytotoxic towards M170 cell line, whereas only 2 out of the 5 clonotypes derived from healthy donors were lytic against this cell line (HD1.21 and HD3.38). These two clonotypes displayed the better EC50 of the 5 clonotypes derived from healthy donors: respectively $10^{-2}$ and $10^{-3}$ μM.

Discussion

Figure 2:
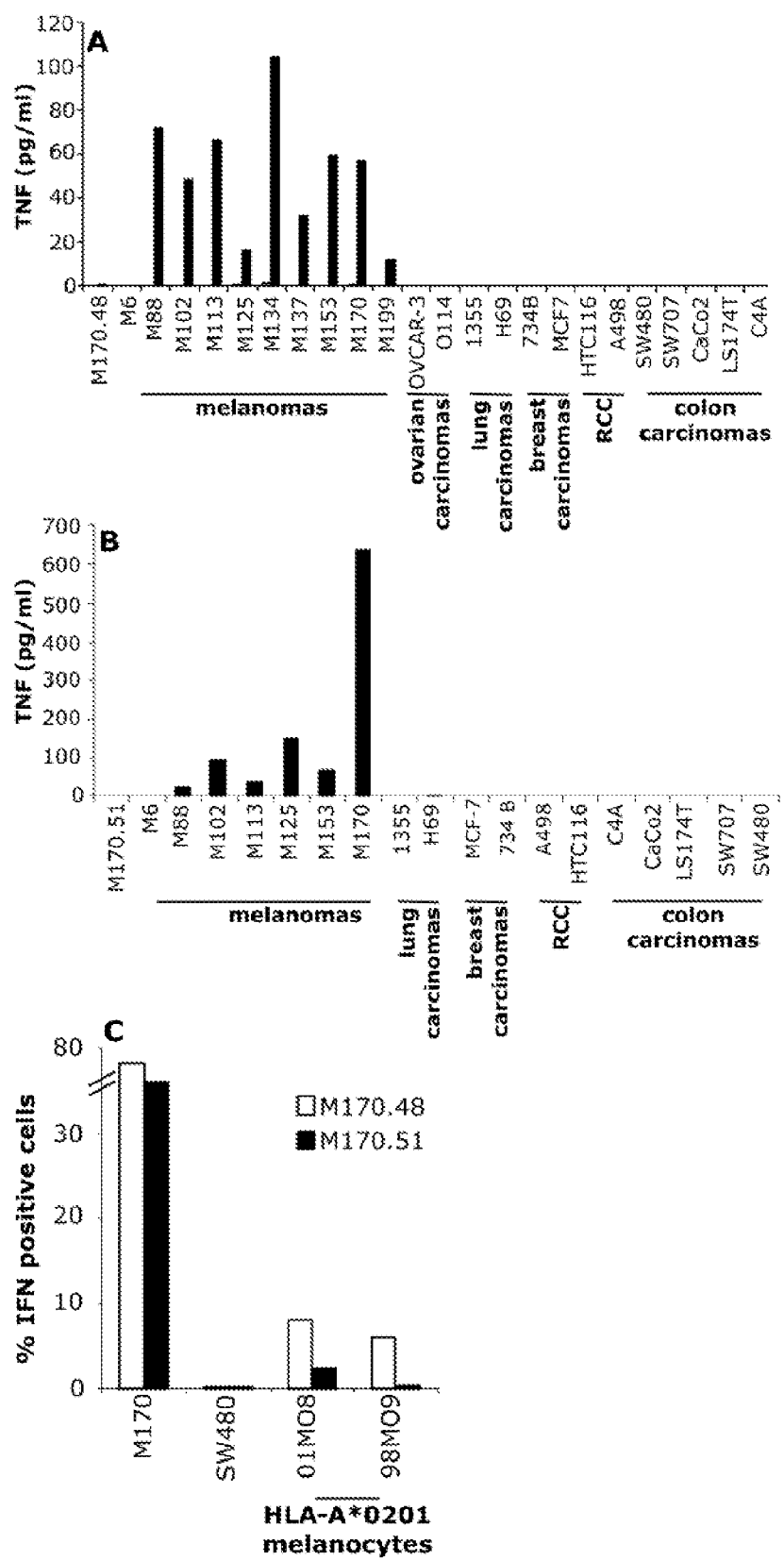
FIG. 2. (A and B) TNF response of M170.48 CTL clone (A) and M170.51 CTL clone (C) to HLA-A*0201 tumor cell lines. M6 cell line, HLA-A2 negative, was used as a negative control. (C) IFN-γ response of M170.48 and M170.51 CTL clones to HLA-A*0201 melanocytes. M170 cell line was added as a positive control.

The meloe gene is located on the third intron of the histone deacetylase-4 gene (HDAC-4), and translated in anti-sense orientation in comparison with the HDAC-4 gene (24). There is a perfect colinearity between the meloe gene and its corresponding cDNA, showing an absence of splicing of this gene. Furthermore, the structure of this 2.1 kb cDNA is rather unusual, with multiple short open reading frames, instead of a unique long ORF. Two proteins respectively encoded by the ORF$_{1230-1370}$ (MELOE-1) and the ORF$_{285-404}$ (MELOE-2) contain peptides that were recognized by CTL clones derived from melanoma specific TIL, in the HLA-A*0201 context. These CTL clones recognized all the HLA-A*0201 melanoma cell lines tested, and to a lower extent HLA-A*0201 melanocytes. On the other hand, these T cell clones failed to recognize any of the other tumor cell lines tested (FIG. 2).

The meloe antigen could be classified into the family of <<melanocytic differentiation antigens>>, due to its expression in melanocytes and melanoma cell lines (25). Nonetheless, it could be also classified into the family of aberrantly expressed antigens, due to the particular location of meloe gene in the third intron of HDAC-4 gene, following the example of NA17-A antigen, located in an intron of the GnT-V gene (6). Uunlike classical differentiation antigens such as Melan-A or tyrosinase (18, 26, 27), we detected by quantitative PCR a residual expression of meloe gene in other cancer cell lines, even if this expression level was too low to induce their recognition by our specific CTL clone, as recently shown for a mouse prostate tumour epitope derived from histone H4 (28). meloe also differs from a classical differentiation antigen by its overexpression in melanomas, compared to normal melanocytes. Thus, meloe seems to be specifically overexpressed in melanomas and therefore, this new antigen presents both the properties of tissue specificity and overexpression in cancer. The reasons of its overexpression in melanomas could be due to the regulation of meloe promoter. As described for MAGE-1 gene, a transient and general process of demethylation in tumors could be followed by a persistent inhibition of remethylation due to the presence of melanoma specific transcription factors (29). In this way, meloe overexpression in melanomas could be due to the hypomethylation of its promoter in melanoma cell lines. In another way, melanoma specific transcription factors, such as MITF which controls the expression of the three main melanocytic differentiation antigens (30, 31), could also control the overexpression of meloe in melanomas.

Due to its expression widely shared by melanoma cell lines, and to the existence of epitopes recognized by melanoma reactive CTL clones in the HLA-A*0201 context, the MELOE-1 and MELOE-2 antigens could be promising targets for future immunotherapy protocols of melanoma, provided that their usage remains safe in patients and that their immunogenicity could be documented.

Our data provides some arguments concerning the safety of immunization of patients with this antigen or of adoptive transfer with specific CTL. Indeed, the expression level of meloe in healthy tissues is always lower than in melanocytes, which are weakly recognized by MELOE-1 and MELOE-2 specific CTL clones, to a lower extent than by Melan-A specific CTL (FIGS. 4C, 1C and data not shown). Furthermore, none of the other HLA-A*0201 cancer cell lines was able to spontaneously induce any reactivity of the two specific CTL (FIG. 2), even after a 48 h-treatment with IFN-γ (data not shown). MELOE-1 specific CTL clone could only be activated by such tumor cell lines when they were previously transfected by the meloe cDNA or the cDNA coding for $ORF_{1230-1370}$ (FIG. 5B), showing that the expression level of meloe in other cancer cell lines was too low to induce the activation of specific lymphocytes. This expression level being similar to that measured in healthy tissues by qPCR (FIG. 5C), this suggests that an immunization with this antigen should not induce deleterious reactions in healthy tissues, although we could expect the induction of some vitiligo due to the expression of meloe in melanocytes.

The second point concerns the immunogenicity of these new antigens and especially the immunogenicity of the HLA-A*0201 restricted epitopes. To answer this main question, we checked the presence of MELOE-1 specific lymphocytes among TIL populations that had been infused to stage III melanoma patients after lymph node excision, in an adjuvant setting. In retrospective studies of this adoptive transfer protocol, we already showed that the infusion of melanoma specific TIL had a significant impact on relapse prevention of treated patient (17). More recently we found that prolonged relapse-free survival of TIL-treated patients correlated with the infusion of Melan-A specific lymphocytes (14), although a significant fraction of tumor-specific TIL remains of unknown specificity in a number of TIL populations infused to relapse-free patients. We detected a significant fraction of MELOE-1 specific lymphocytes, by tetramer labeling, in 5/9 TIL populations infused to HLA-A2 patients who remained relapse-free since 7 to 13 years, whereas no MELOE-1 specific lymphocytes could be observed in 21 TIL populations infused to patients who relapsed. Interestingly, we also found MELOE-2 reactive TIL in M170 and M278 TIL populations (data not shown). The statistical analysis of these results performed by a $Chi^2$ test, documents a correlation between the prevention of relapse of TIL treated HLA-A2 patients and the presence of MELOE-1 specific CTLs among those TIL ($p<0.001$). This main result provides a strong argument in favor of the implication of MELOE-1 antigen in the immunosurveillance of patients treated by adoptive transfer of TIL. This role in immunosurveillance has not been formally elucidated for the majority of melanoma antigens identified, except for Melan-A/MART-1, which seems clearly involved in clinical responses of melanoma patients treated by immunotherapy (10-12, 14, 15). Following the example of Melan-A antigen, a diverse and tumor reactive T cell repertoire is necessary to develop protocols of adoptive transfer of specific T cells in melanoma patients, and also for vaccination trials. We addressed this last issue by analyzing the diversity and reactivity of MELOE-1 specific repertoire in the 5 TIL populations that contained MELOE-1 specific T cells. After selection of MELOE-1 specific T cells from TIL by immunomagnetic sorting with multimer-coated beads (23), we showed that MELOE-1 specific repertoire was diverse in 3/5 TIL populations, and much more limited for M134 TIL population, which contained a low fraction of MELOE-1 specific T cells (FIGS. 6A and 6B), that could explain this poorer diversity. We could not determine the dominant Vβ chain(s) expressed by M180 sorted TIL with our panel of antibodies (FIG. 6B). The repertoire analysis of these TIL populations did not reveal any recurrence of a particular Vβ usage, as previously described for Melan-A specific repertoire (23). These five MELOE-1 specific TIL populations were as reactive as the M170.48 specific T cell clone against HLA-A2 melanoma cell lines, as shown by lysis (FIG. 7A) and IFN-γ and TNF-β production in response to melanoma cells, and, to a lower extent, IL-2 production (FIG. 7B). Furthermore, we recently demonstrated that MELOE-1 specific T cells could be also selected and amplified from PBMC of melanoma patients (data not shown), that remains the most convenient source of tumor specific T cells usable for all HLA-A2 patients enrolled in adoptive transfer protocols.

Using a method recently described of tetramer enrichment (42), we have enumerated and phenotyped ex-vivo MELOE-1 specific T cells present in HLA-A2 healthy donors and patient peripheral blood. Results show that MELOE-1 specific T cells are present in each healthy donor and patient, at similar frequencies : around $10^{-5}$ among $CD8^+$ cells. This frequency in around ten times lower than the frequency of Melan-A specific T cells. With the exception of the Melan-A antigen, few studies have established ex-vivo frequencies of tumor antigen specific T cells in peripheral blood, their low frequencies precluding their direct evaluation. Nonetheless, frequencies of MAGE-3/A1 specific T cells have been evaluated in healthy donors by a limiting dilution approach and reveal a frequency as low as $2.10^{-7}$ among $CD8^+$ T cells. This frequency ranged between $7.10^{-7}$ and $3.10^{-3}$ in patients who were immune responders to a vaccination with a recombinant virus encoding the antigen, while this frequency remains around $5.10^{-7}$ in non responder patients (45). The only study reporting a high frequency of CTL specific for a tumor specific antigen concerns CTLs specific for NY-ESO-1 antigen (around $2.10^{-4}$ among $CD8^+$), observed in only one melanoma patient (46). Therefore, the presence of MELOE-1 specific T cells in HLA-A2 melanoma patients, with a frequency around $10^{-5}$ among $CD8^+$ lymphocytes supports the development of immunotherapy protocols targeting this antigen, and this is strengthened by a recent study demonstrating the functional relevance of $CD8^+$ precursor frequency to tumor immunity (47).

REFERENCES

All the cited references are incorporated by reference.
1. Kawakami, Y., S. Eliyahu, C. H. Delgado, P. F. Robbins, K. Sakaguchi, E. Appella, J. R. Yannelli, G. J. Adema, T. Miki, and S. A. Rosenberg. 1994. Identification of a human melanoma antigen recognized by tumor-infiltrating lymphocytes associated with in vivo tumor rejection. *Proc Natl Acad Sci USA* 91:6458-6462.
2. Van der Bruggen, P., C. Traversari, P. Chomez, C. Lurquin, E. De Plaen, B. Van den Eynde, A. Knuth, and T. Boon. 1991. A gene encoding an antigen recognized by cytolytic T lymphocytes on a human melanoma. *Science* 254:1643-1647.
3. Gaugler, B., B. Van den Eynde, P. van der Bruggen, P. Romero, J. J. Gaforio, E. De Plaen, B. Lethe, F. Brasseur, and T. Boon. 1994. Human gene MAGE-3 codes for an antigen recognized on a melanoma by autologous cytolytic T lymphocytes. *J Exp Med* 179:921-930.
4. Wolfel, T., M. Hauer, J. Schneider, M. Serrano, C. Wolfel, E. Klehmann-Hieb, E. De Plaen, T. Hankeln, K. H. Meyer zum Buschenfelde, and D. Beach. 1995. A p16INK4a-insensitive CDK4 mutant targeted by cytolytic T lymphocytes in a human melanoma. *Science* 269:1281-1284.
5. Kessler, J. H., N. J. Beekman, S. A. Bres-Vloemans, P. Verdijk, P. A. van Veelen, A. M. Kloosterman-Joosten, D. C. Vissers, G. J. ten Bosch, M. G. Kester, A. Sijts, et al. 2001. Efficient identification of novel HLA-A(*)0201-presented cytotoxic T lymphocyte epitopes in the widely expressed tumor antigen PRAME by proteasome-mediated digestion analysis. *J Exp Med* 193:73-88.
6. Guilloux, Y., S. Lucas, V. G. Brichard, A. Van Pel, C. Viret, E. De Plaen, F. Brasseur, B. Lethe, F. Jotereau, and T. Boon. 1996. A peptide recognized by human cytolytic T lymphocytes on HLA-A2 melanomas is encoded by an intron sequence of the N-acetylglucosaminyltransferase V gene. *J Exp Med* 183:1173-1183.
7. Moreau-Aubry, A., S. Le Guiner, N. Labarriere, M. C. Gesnel, F. Jotereau, and R. Breathnach. 2000. A processed pseudogene codes for a new antigen recognized by a CD8(+) T cell clone on melanoma. *J Exp Med* 191:1617-1624.
8. Jager, E., M. Maeurer, H. Hohn, J. Karbach, D. Jager, Z. Zidianakis, A. Bakhshandeh-Bath, J. Orth, C. Neukirch, A. Necker, et al. 2000. Clonal expansion of Melan A-specific cytotoxic T lymphocytes in a melanoma patient responding to continued immunization with melanoma-associated peptides. *Int J Cancer* 86:538-547.
9. Jager, E., H. Hohn, A. Necker, R. Forster, J. Karbach, K. Freitag, C. Neukirch, C. Castelli, R. D. Salter, A. Knuth, et al. 2002. Peptide-specific CD8+ T-cell evolution in vivo: response to peptide vaccination with Melan-A/MART-1. *Int J Cancer* 98:376-388.
10. Dudley, M. E., J. R. Wunderlich, P. F. Robbins, J. C. Yang, P. Hwu, D. J. Schwartzentruber, S. L. Topalian, R. Sherry, N. P. Restifo, A. M. Hubicki, et al. 2002. Cancer regression and autoimmunity in patients after clonal repopulation with antitumor lymphocytes. *Science* 298:850-854.
11. Mackensen, A., N. Meidenbauer, S. Vogl, M. Laumer, J. Berger, and R. Andreesen. 2006. Phase I study of adoptive T-cell therapy using antigen-specific CD8+ T cells for the treatment of patients with metastatic melanoma. *J Clin Oncol* 24:5060-5069.
12. Meidenbauer, N., J. Marienhagen, M. Laumer, S. Vogl, J. Heymann, R. Andreesen, and A. Mackensen. 2003. Survival and tumor localization of adoptively transferred Melan-A-specific T cells in melanoma patients. *J Immunol* 170:2161-2169.
13. Vignard, V., B. Lemercier, A. Lim, M. C. Pandolfino, Y. Guilloux, A. Khammari, C. Rabu, K. Echasserieau, F. Lang, M. L. Gougeon, et al. 2005. Adoptive transfer of tumor-reactive Melan-A-specific CTL clones in melanoma patients is followed by increased frequencies of additional Melan-A-specific T cells. *J Immunol* 175:4797-4805.
14. Benlalam, H., V. Vignard, A. Khammari, A. Bonnin, Y. Godet, M. C. Pandolfino, F. Jotereau, B. Dreno, and N. Labarriere. 2007. Infusion of Melan-A/Mart-1 specific tumor-infiltrating lymphocytes enhanced relapse-free survival of melanoma patients. *Cancer Immunol Immunother* 56:515-526.
15. Yee, C., J. A. Thompson, D. Byrd, S. R. Riddell, P. Roche, E. Celis, and P. D. Greenberg. 2002. Adoptive T cell therapy using antigen-specific CD8+ T cell clones for the treatment of patients with metastatic melanoma: in vivo persistence, migration, and antitumor effect of transferred T cells. *Proc Natl Acad Sci USA* 99:16168-16173.
16. Dreno, B., J. M. Nguyen, A. Khammari, M. C. Pandolfino, M. H. Tessier, S. Bercegeay, A. Cassidanius, P. Lemarre, S. Billaudel, N. Labarriere, et al. 2002. Randomized trial of adoptive transfer of melanoma tumor-infiltrating lymphocytes as adjuvant therapy for stage III melanoma. *Cancer Immunol Immunother* 51:539-546.
17. Labarriere, N., M. C. Pandolfino, N. Gervois, A. Khammari, M. H. Tessier, B. Dreno, and F. Jotereau. 2002. Therapeutic efficacy of melanoma-reactive TIL injected in stage III melanoma patients. *Cancer Immunol Immunother* 51:532-538.
18. Khammari, A., J. M. Nguyen, M. C. Pandolfino, G. Quereux, A. Brocard, S. Bercegeay, A. Cassidanius, P. Lemarre, C. Volteau, N. Labarriere, et al. 2007. Long-term follow-up of patients treated by adoptive transfer of melanoma tumor-infiltrating lymphocytes as adjuvant therapy for stage III melanoma. *Cancer Immunol Immunother* 56:1853-1860.
19. Benlalam, H., N. Labarriere, B. Linard, L. Derre, E. Diez, M. C. Pandolfino, M. Bonneville, and F. Jotereau. 2001. Comprehensive analysis of the frequency of recognition of melanoma-associated antigen (MAA) by CD8 melanoma infiltrating lymphocytes (TIL): implications for immunotherapy. *Eur J Immunol* 31:2007-2015.
20. Godefroy, E., A. Moreau-Aubry, E. Diez, B. Dreno, F. Jotereau, and Y. Guilloux. 2005. alpha v beta3-dependent cross-presentation of matrix metalloproteinase-2 by melanoma cells gives rise to a new tumor antigen. *J Exp Med* 202:61-72.
21. Strausberg, R. L., E. A. Feingold, L. H. Grouse, J. G. Derge, R. D. Klausner, F. S. Collins, L. Wagner, C. M. Shenmen, G. D. Schuler, S. F. Altschul, et al. 2002. Generation and initial analysis of more than 15,000 full-length human and mouse cDNA sequences. *Proc Natl Acad Sci USA* 99:16899-16903.

22. Venter, J. C., M. D. Adams, E. W. Myers, P. W. Li, R. J. Mural, G. G. Sutton, H. O. Smith, M. Yandell, C. A. Evans, R. A. Holt, et al. 2001. The sequence of the human genome. *Science* 291:1304-1351.
23. Labarriere, N., N. Gervois, A. Bonnin, R. Bouquie, F. Jotereau, and F. Lang. 2008. PBMC are as good a source of tumor-reactive T lymphocytes as TIL after selection by Melan-A/A2 multimer immunomagnetic sorting. *Cancer Immunol Immunother* 57:185-195.
24. Grozinger, C. M., C. A. Hassig, and S. L. Schreiber. 1999. Three proteins define a class of human histone deacetylases related to yeast Hdalp. *Proc Natl Acad Sci USA* 96:4868-4873.
25. Boon, T., P. G. Coulie, B. J. Van den Eynde, and P. van der Bruggen. 2006. Human T cell responses against melanoma. *Annu Rev Immunol* 24:175-208.
26. Coulie, P. G., V. Brichard, A. Van Pel, T. Wolfel, J. Schneider, C. Traversari, S. Mattei, E. De Plaen, C. Lurquin, J. P. Szikora, et al. 1994. A new gene coding for a differentiation antigen recognized by autologous cytolytic T lymphocytes on HLA-A2 melanomas. *J Exp Med* 180:35-42.
27. Brichard, V., A. Van Pel, T. Wolfel, C. Wolfel, E. De Plaen, B. Lethe, P. Coulie, and T. Boon. 1993. The tyrosinase gene codes for an antigen recognized by autologous cytolytic T lymphocytes on HLA-A2 melanomas. *J Exp Med* 178:489-495.
28. Savage, P. A., K. Vosseller, C. Kang, K. Larimore, E. Riedel, K. Wojnoonski, A. A. Jungbluth, and J. P. Allison. 2008. Recognition of a ubiquitous self antigen by prostate cancer-infiltrating CD8+ T lymphocytes. *Science* 319:215-220.
29. De Smet, C., A. Loriot, and T. Boon. 2004. Promoter-dependent mechanism leading to selective hypomethylation within the 5' region of gene MAGE-A1 in tumor cells. *Mol Cell Biol* 24:4781-4790.
30. Du, J., A. J. Miller, H. R. Widlund, M. A. Horstmann, S. Ramaswamy, and D. E. Fisher. 2003. MLANA/MART1 and SILV/PMEL17/GP100 are transcriptionally regulated by MITF in melanocytes and melanoma. *Am J Pathol* 163:333-343.
31. Bentley, N. J., T. Eisen, and C. R. Goding. 1994. Melanocyte-specific expression of the human tyrosinase promoter: activation by the microphthalmia gene product and role of the initiator. *Mol Cell Biol* 14:7996-8006.
32. Pandolfino, M. C., N. Labarriere, M. H. Tessier, A. Cassidanius, S. Bercegeay, P. Lemarre, F. Dehaut, B. Dreno, and F. Jotereau. 2001. High-scale expansion of melanoma-reactive TIL by a polyclonal stimulus: predictability and relation with disease advancement. *Cancer Immunol Immunother* 50:134-140.
33. Jotereau, F., M. C. Pandolfino, D. Boudart, E. Diez, B. Dreno, J. Y. Douillard, J. Y. Muller, and B. LeMevel. 1991. High-fold expansion of human cytotoxic T-lymphocytes specific for autologous melanoma cells for use in immunotherapy. *J Immunother* (1991) 10:405-411.
34. Gervois, N., N. Labarriere, S. Le Guiner, M. C. Pandolfino, J. F. Fonteneau, Y. Guilloux, E. Diez, B. Dreno, and F. Jotereau. 2000. High avidity melanoma-reactive cytotoxic T lymphocytes are efficiently induced from peripheral blood lymphocytes on stimulation by peptide-pulsed melanoma cells. *Clin Cancer Res* 6:1459-1467.
35. Espevik, T., and J. Nissen-Meyer. 1986. A highly sensitive cell line, WEHI 164 clone 13, for measuring cytotoxic factor/tumor necrosis factor from human monocytes. *J Immunol Methods* 95:99-105.
36. Jung, T., U. Schauer, C. Heusser, C. Neumann, and C. Rieger. 1993. Detection of intracellular cytokines by flow cytometry. *J Immunol Methods* 159:197-207.
37. Pfaffl, M. W., I. G. Lange, A. Daxenberger, and H. H. Meyer. 2001. Tissue-specific expression pattern of estrogen receptors (ER): quantification of ER alpha and ER beta mRNA with real-time RT-PCR. *Apmis* 109:345-355.
38. Bodinier, M., M. A. Peyrat, C. Tournay, F. Davodeau, F. Romagne, M. Bonneville, and F. Lang. 2000. Efficient detection and immunomagnetic sorting of specific T cells using multimers of MHC class I and peptide with reduced CD8 binding. *Nat Med* 6:707-710.
39. Hans-Georg Rammensee, Thomas Friede and Stefan Stevanović. 1995. MHC ligands and peptide motifs: first listing *Immunogenetics,* 41:178.
40. Sudo T, Kamikawaji N, Kimura A, Date Y, Savoie C J, Nakashima H, Furuichi E, Kuhara S, Sasazuki T. 1995. Differences in MHC class I self peptide repertoires among HLA-A2 subtypes. *J. Immunol,* 155:4749-4756.
41. Coulie P, Somville M, Lehmann F, Hainaut P, Brasseur F, Devos R, Boon T. 1992. Precursor frequency analysis of human cytolytic T lymphocytes directed against autologous melanoma cells. *International Journal of Cancer* 50:289-294
42. Moon J J, Chu H H, Pepper M, et al. Naive CD4(+) T cell frequency varies for different epitopes and predicts repertoire diversity and response magnitude. Immunity 2007; 27:203-13.
43. Klebanoff C A, Gattinoni L, Torabi-Parizi P, et al. Central memory self/tumor-reactive CD8+ T cells confer superior antitumor immunity compared with effector memory T cells. Proc Natl Acad Sci USA 2005; 102:9571-6.
44. Klebanoff C A, Gattinoni L, Restifo N P. CD8+ T-cell memory in tumor immunology and immunotherapy. Immunol Rev 2006; 211:214-24.
45. Lonchay C, van der Bruggen P, Connerotte T, et al. Correlation between tumor regression and T cell responses in melanoma patients vaccinated with a MAGE antigen. Proc Natl Acad Sci USA 2004; 101:14631-8.
46. Valmori D, Dutoit V, Liénard D, et al. Naturally occurring human lymphocyte antigen-A2 restricted CD8+ T-cell response to the cancer testis antigen NY-ESO-1 in melanoma patients. Cancer Res 2000; 60:4499-506.
47. Rizzuto G A, Merghoub T, Hirschhorn-Cymerman D, et al. Self-antigen-specific CD8+ T cell precursor frequency determines the quality of the antitumor immune response. J Exp Med 2009; 206:849-66.

The invention claimed is:

1. A melanoma antigen peptide having an amino acid sequence that is less than 50 amino acids in length and comprising SEQ ID NO:2:

```
TX₂NDECWPX₉          (SEQ ID NO: 2)
``` wherein $X_2$ is leucine, methionine, valine, isoleucine or glutamine and $X_9$ is alanine, valine or leucine.

2. A melanoma antigen peptide according to claim 1, wherein said melanoma antigen peptide is MELOE-1 having the sequence SEQ ID NO: 4.

3. A melanoma antigen peptide according to claim 1, wherein said melanoma antigen peptide is selected in the group consisting of peptides having the sequence SEQ ID NO: 6 to SEQ ID NO: 20.

4. A MHC/peptide multimer comprising a melanoma antigen peptide according to claim 3.

5. An immunising composition comprising
at least one melanoma antigen peptide according to claim 1.

* * * * *

UNITED STATES PATENT AND TRADEMARK OFFICE
CERTIFICATE OF CORRECTION

PATENT NO. : 8,604,166 B2
APPLICATION NO. : 13/060484
DATED : December 10, 2013
INVENTOR(S) : Labarriere et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 248 days.

Signed and Sealed this
Twenty-third Day of May, 2017

Michelle K. Lee
*Director of the United States Patent and Trademark Office*